(12) United States Patent
Henry et al.

(10) Patent No.: US 11,406,314 B2
(45) Date of Patent: Aug. 9, 2022

(54) METHOD AND SYSTEM FOR MONITORING A PATIENT FOR ATRIAL FIBRILLATION AND/OR ASYSTOLE

(71) Applicant: SOTERA WIRELESS, INC., San Diego, CA (US)

(72) Inventors: Isaac Henry, San Diego, CA (US); Devin McCombie, Carlsbad, CA (US); Nicholas Elmschig, Tiburon, CA (US)

(73) Assignee: SOTERA WIRELESS, INC., San Diego, CA (US)

( * ) Notice: Subject to any disclaimer, the term of this patent is extended or adjusted under 35 U.S.C. 154(b) by 193 days.

(21) Appl. No.: 16/580,958

(22) Filed: Sep. 24, 2019

(65) Prior Publication Data
US 2020/0093389 A1 Mar. 26, 2020

Related U.S. Application Data

(60) Provisional application No. 62/735,793, filed on Sep. 24, 2018.

(51) Int. Cl.
| | |
|---|---|
| *A61B 5/366* | (2021.01) |
| *A61B 5/361* | (2021.01) |
| *A61B 5/00* | (2006.01) |
| *A61B 5/024* | (2006.01) |
| *A61B 5/282* | (2021.01) |
| *A61B 5/339* | (2021.01) |
| *A61B 5/363* | (2021.01) |
| *A61B 5/11* | (2006.01) |

(52) U.S. Cl.
CPC ............ *A61B 5/361* (2021.01); *A61B 5/0006* (2013.01); *A61B 5/02416* (2013.01); *A61B 5/282* (2021.01); *A61B 5/339* (2021.01); *A61B 5/363* (2021.01); *A61B 5/366* (2021.01); *A61B 5/1118* (2013.01)

(58) Field of Classification Search
CPC ......... A61B 5/361; A61B 5/349; A61B 5/366; A61B 5/352
See application file for complete search history.

(56) References Cited

U.S. PATENT DOCUMENTS

| | | |
|---|---|---|
| 2016/0287122 A1 | 10/2016 | Heneghan |
| 2016/0345844 A1 | 12/2016 | Mccombie et al. |
| 2017/0027456 A1 | 2/2017 | Kinast et al. |
| 2018/0021581 A1 | 1/2018 | An et al. |
| 2018/0235537 A1 | 8/2018 | Whiting et al. |

OTHER PUBLICATIONS

The International Search Report and Written Opinion issued in PCT/US2019/052706 dated Feb. 3, 2020 (13 pages).
Alcaraz and Rieta, A review on sample entropy applications of the non-invasive analysis of atrial fibrillation electrocardiograms. Biomedical Signal Processing and Control; 2010; 5:1-14.
Arafat et al., A simple time domain algorithm for detection of ventricular fibrillation in electrocardiogram. Signal Image and Video Processing; Mar. 2011;5(1):1-10.

(Continued)

*Primary Examiner* — Michael J D'abreu
(74) *Attorney, Agent, or Firm* — Acuity Law Group, PC; Michael A. Whittaker

(57) ABSTRACT

Methods and systems methods for continuously monitoring a patient for cardiac electrical abnormalities including atrial fibrillation, asystole, ventricular fibrillation and tachycardia.

26 Claims, 18 Drawing Sheets

(56) References Cited

OTHER PUBLICATIONS

Arzeno et al., Analysis of First-Derivative Based QRS Detection Algorithms. IEEE Trans Biomed Eng Feb. 2008;55(2 Pt 1):478-484.
Cheng and Dong, Life-Threatening Ventricular Arrhythmia Detection With Personalized Features. IEEE Access, 2017;5:14195-14203, doi:10.1109/ACCESS.2017.2723258.
Dash et al., Automatic Real Time Detection of Atrial Fibrillation. Ann Biomed Eng. Sep. 2009;37(9):1701-1709.
Hamilton and Tompkins, Quantitative Investigation of QRS Detection Rules Using the MIT/BIH Arrhythmia Database. IEEE Trans Biomed Eng. Dec. 1986;33(12):1157-1165.
Jekova and Krasteva, Real Time detection of ventricular fibrillation and tachycardia. Physiol Meas. Oct. 2004;25(5):1167-1178.
Jekova, Shock advisory tool: Detection of life threatening cardiac arrhythmias and shock success prediction by means of a common parameter set. Biomedical Signal Processing and Control; Jan. 2007;2(1):25-33.
Li et al., Detecting Ventricular Fibrillation by Fast Algorithm of Dynamic Sample Entropy. Proceedings of the 2009 IEEE International Conference on Robotics and Biomimetics; 2009: 1105-1110.
Li et al., Ventricular Fibrillation and Tachycardia Classification Using a Machine Learning Approach. IEEE Trans Biomed Eng. Jun. 2014;61(6):1607-1613.
Pan and Tompkins, A Real-Time QRS Detection Algorithm. IEEE Trans Biomed Eng. Mar. 1985;32(3):230-236.
Tabakov et al., Online Digital Filter and QRS Detector Applicable in Low Resource ECG Monitoring Systems. Ann Biomed Eng. Nov. 2008;36(11):1805-1815.
Zhu et al., Multi-class AdaBoost. Statistics and Its Interface; 2009;2:349-360.

METHOD AND SYSTEM FOR MONITORING A PATIENT FOR ATRIAL FIBRILLATION AND/OR ASYSTOLE

The present application claims benefit of U.S. Provisional Application No. 62/735,793, filed Sep. 24, 2018, which is hereby incorporated by reference in its entirety including all tables, figures, and claims and from which priority is claimed.

BACKGROUND OF THE INVENTION

Atrial fibrillation (AF) is a supraventricular tachyarrhythmia with uncoordinated atrial activation and consequently ineffective atrial contraction. Characteristics on an electrocardiogram (ECG) include 1) irregular R-R intervals (when atrioventricular (AV) conduction is present), 2) absence of distinct repeating P waves, and 3) irregular atrial activity. AF may be triggered by potentially reversible, or acute, causes such as surgery (cardiac and noncardiac), hyperthyroidism, myocarditis or pericarditis, myocardial infarction, pulmonary embolism, pneumonia, and alcohol intoxication.

While loop recorders, pacemakers, and defibrillators offer the possibility of reporting frequency, rate, and duration of abnormal atrial rhythms, including AF, a challenge to the use of body-worn AF monitors for continuous monitoring and reporting of AF arises from noise and artifacts prevalent in ambulatory monitors, resulting in false alarms, irrelevant data that is incorrectly identified for analysis, and a resulting alarm fatigue.

SUMMARY OF THE INVENTION

This invention provides a method and body-worn system for continuously monitoring a patient for cardiac electrical abnormalities including ventricular fibrillation/tachycardia, AF and/or asystole.

In a first aspect, the invention relates to methods for continuously monitoring a patient for cardiac electrical abnormalities, comprising:

obtaining a plurality of time-dependent electrocardiogram (ECG) waveforms from an ECG sensor comprising plurality of ECG electrodes, each waveform in the plurality of waveforms corresponding to electrical signals obtained from one ECG electrode in the plurality of ECG electrodes;

processing the plurality of waveforms by
  determining a time-dependent first signal quality parameter for each waveform in the plurality of waveforms and curating the plurality of waveforms by comparing each first signal quality parameter to a first quality threshold metric,
  wherein if at least one first signal quality parameter exceeds the first quality threshold metric, accepting those waveforms having a first signal quality parameter that exceed the first quality threshold metric and discarding those waveforms having a first signal quality parameter that does not exceed the first quality threshold metric, or if no first signal quality parameter exceeds the first quality threshold metric, accepting all waveforms, and
  combining the accepted waveforms to provide a time-dependent combined ECG waveform;
processing the combined ECG waveform to by
  identifying each QRS complex in the combined ECG waveform,
  determining a second signal quality parameter for each QRS complex by gravity cliff detection, and
  curating each second signal quality parameter by comparing each second signal quality parameter to a second quality threshold metric, wherein if the second signal quality parameter exceeds the second quality threshold metric, the QRS complex is identified as a valid QRS complex;
determining the occurrence or nonoccurrence of asystole and/or atrial fibrillation from the valid QRS complexes; and
causing an alarm to be displayed on a display component when asystole and/or atrial fibrillation is determined to occur.

In certain embodiments, the accepted waveforms are combined to provide a time-dependent combined ECG waveform by averaging of the accepted waveforms.

In certain embodiments the method comprises determining the occurrence or nonoccurrence of asystole, wherein asystole is determined to occur when no valid QRS complexes are identified over a predetermined time period.

In still other embodiments, the method comprises determining the occurrence or nonoccurrence of atrial fibrillation, wherein atrial fibrillation is determined by, for a plurality of pairs of consecutive valid QRS complexes occurring over a predetermined time period,
  for each consecutive pair of valid QRS complexes, determining an interval between a first fiducial point in the first member of the consecutive pair to a corresponding fiducial point in the first member of the consecutive pair, thereby providing a plurality of intervals,
  curating the plurality of intervals by calculating a third signal quality parameter for each interval and comparing each third signal quality parameter to a third quality threshold metric, wherein if the third signal quality parameter exceeds the third quality threshold metric, the interval is identified as a valid interval, and
  classifying whether the valid intervals obtained from the plurality of pairs of consecutive valid QRS complexes are indicative of atrial fibrillation.

In various embodiments, the classifying step comprises calculating a root mean square of successive differences in the valid intervals; calculating a sample entropy of successive differences in the valid intervals; or both. By way of example, the classifying step may comprise calculating a two dimensional space that is a function of a root mean square of successive differences in the valid intervals and a sample entropy of successive differences in the valid intervals, and defining values that fall within an area or multiple areas within the two dimensional space as being indicative of the occurrence of atrial fibrillation.

In certain embodiments, the method further comprises determining the occurrence or nonoccurrence of ventricular fibrillation/tachycardia. Such determination may comprise the following steps:
processing at least two of the plurality of time-dependent ECG waveforms by
  selecting from each of the at least two ECG waveforms, a first waveform segment of time length t, and a second waveform segment of time length t, wherein the first and second waveform segments are non-overlapping consecutive segments, and
  for each of the first and second waveform segments, calculating a four-dimensional feature space comprising at least one temporal feature, at least one spectral feature, and at least one a complexity feature;

for each of the at least two ECG waveforms, determining if the four-dimensional feature space is indicative of the occurrence of ventricular fibrillation/tachycardia, wherein if ventricular fibrillation/tachycardia is indicated by processing of each of the at least two ECG waveforms, the occurrence ventricular fibrillation/tachycardia is determined; and cause an alarm to be displayed on a display component when ventricular fibrillation/tachycardia is determined to occur.

By way of example, the four-dimensional feature space may comprise threshold crossing sample count (TCSC), VF filter (VFleak), sample entropy, and Count2 features. This list is not meant to be limiting, and other temporal, spectral, and complexity features are known in the art. See, e.g., Cheng and Dong, Digital Object Identifier 10.1109/AC-CESS.2017.2723258.

In certain embodiments, the first signal quality parameter is a kurtosis value calculated for each waveform in the plurality of waveforms. The term "kurtosis" refers to the a measure of the shape of a set of data, in this case of a frequency-distribution curve. More specifically, kurtosis measures the relative peakedness of a distribution with respect to a Gaussian distribution. In preferred embodiments, the kurtosis value for each waveform in the plurality of waveforms is calculated from a time window of a predetermined length in each waveform. By way of example only, the kurtosis value for each waveform may updated at an interval of between 2 and 20 seconds, and preferably about every 3 to about every 5 seconds. These intervals may be overlapping or consecutive.

In certain embodiments, the second signal quality parameter is determined using a "cliff amplitude" (i.e., the signal amplitude at the point of detection) and an elapsed time since the previous valid QRS complex identified. Methods for determining the second signal quality parameter are described hereinafter.

The skilled artisan will understand that many approaches are available for QRS detection. First-derivative-based methods are often used in real-time analysis or for large datasets since they do not require extensive computations. These methods also have the advantage of not necessitating manual segmentation of data, training of the algorithms, or patient-specific modifications that are often required for other detection methods. In certain embodiments, QRS complexes in the combined ECG waveform may be determined using a so-called Pan-Tompkins algorithm or a variation thereof. See, e.g., Pan and Tompkins, IEEE Trans. Eng. Biomed. Eng., 32: 230-36, 1985; Hamilton and Tompkins, IEEE Trans. Eng. Biomed. Eng. 12: 1157-1165, 1986; Arzeno et al., IEEE Trans. Eng. Biomed. Eng. 55: 478-84, 2008.

In a related aspect, the invention relates to methods for continuously monitoring a patient for cardiac electrical abnormalities, comprising:

obtaining a plurality of time-dependent electrocardiogram (ECG) waveforms from an ECG sensor comprising plurality of ECG electrodes, each waveform in the plurality of waveforms corresponding to electrical signals obtained from one ECG electrode in the plurality of ECG electrodes;

processing the plurality of waveforms by
 determining a time-dependent first signal quality parameter for each waveform in the plurality of waveforms and curating the plurality of waveforms by comparing each first signal quality parameter to a first quality threshold metric, wherein if at least one first signal quality parameter exceeds the first quality threshold metric, accepting those waveforms having a first signal quality parameter that exceed the first quality threshold metric and discarding those waveforms having a first signal quality parameter that does not exceed the first quality threshold metric, or if no first signal quality parameter exceeds the first quality threshold metric, accepting all waveforms, and combining the accepted waveforms to provide a time-dependent combined ECG waveform.

In a further related aspect, the present invention provides systems adapted for continuously monitoring a patient for cardiac electrical abnormalities according to the foregoing methods. Such systems comprise:

an ECG sensor comprising plurality of ECG electrodes configured to be worn on the patient's body, the sensor configured to generate a plurality of time-dependent ECG waveforms, each waveform in the plurality of waveforms corresponding to electrical signals obtained from one ECG electrode in the plurality of ECG electrodes;

a processing component configured to receive and process the plurality of time-dependent ECG waveforms by
 determining a time-dependent first signal quality parameter for each waveform in the plurality of waveforms and curating the plurality of waveforms by comparing each first signal quality parameter to a first quality threshold metric, wherein if at least one first signal quality parameter exceeds the first quality threshold metric, accepting those waveforms having a first signal quality parameter that exceed the first quality threshold metric and discarding those waveforms having a first signal quality parameter that does not exceed the first quality threshold metric, or if no first signal quality parameter exceeds the first quality threshold metric, accepting all waveforms, and combining the accepted waveforms to provide a time-dependent combined ECG waveform;

the processing component further configured to process the combined ECG waveform to by
 identifying each QRS complex in the combined ECG waveform,
 determining a second signal quality parameter for each QRS complex by gravity cliff detection,
 curating each second signal quality parameter by comparing each second signal quality parameter to a second quality threshold metric, wherein if the second signal quality parameter exceeds the second quality threshold metric, the QRS complex is identified as a valid QRS complex;
 determining the occurrence or nonoccurrence of asystole and/or atrial fibrillation from the valid QRS complexes; and cause an alarm to be displayed on a display component when asystole and/or atrial fibrillation is determined to occur.

DETAILED DESCRIPTION OF THE INVENTION

System Overview

For purposes of the present application, the following abbreviations apply:

| Terminology | Definition |
|---|---|
| ECG | Electrocardiogram |
| ASYS | Asystole |
| AFIB or AF | Atrial Fibrillation |
| VFIB or VF | Ventricular Fibrillation |
| VTACH | Ventricular Tachycardia |
| LTA + AF | Life Threatening Arrhythmias plus Atrial Fibrillation |
| RR | Interval between successive QRS complexes |
| HR | Heart Rate |
| PPV | Positive Predictive Value |
| PPG | Photoplethysmogram |
| PI | Pulse Interval |
| ACC | Accelerometer |
| PWD | Patient Worn Device |
| RVD | Remote Viewing Device |
| RMSSD | Root mean square of successive differences |
| SAMPEN | Sample Entropy |

Figure 1:
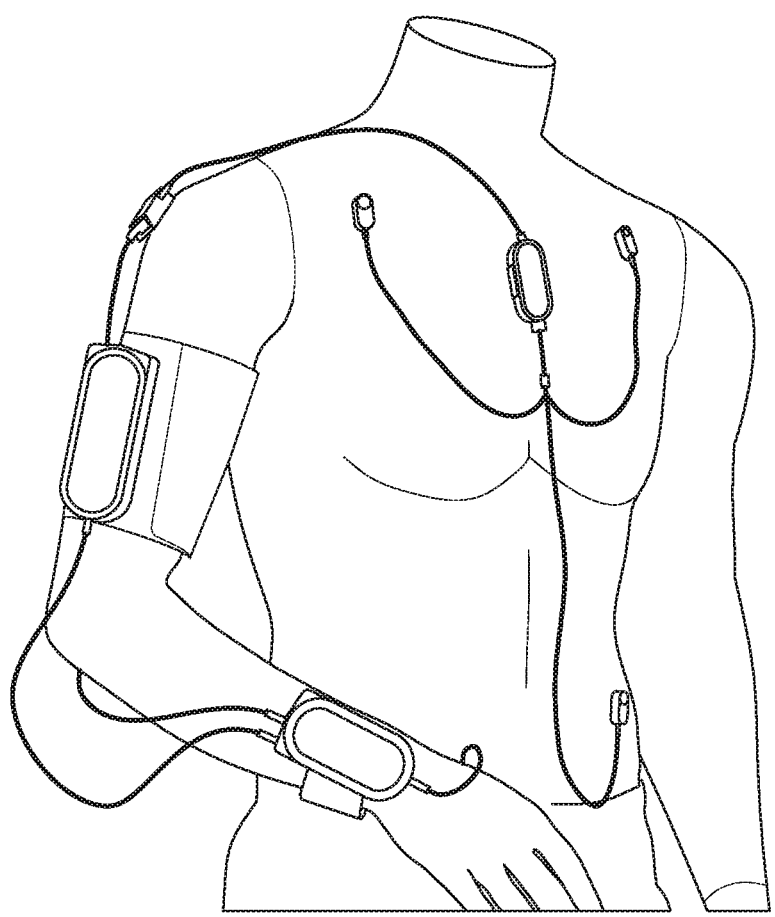
FIG. 1 depicts an exemplary body worn vital signs monitoring system.

For purposes of example only, the present invention is described in terms of using the ViSi Mobile® vital sign monitoring system (Sotera Wireless, Inc.). The ViSi Mobile system is a body-worn vital sign monitor that continuously measures heart rate, SpO2, respiration rate, pulse rate, blood pressure, and skin temperature. The body worn monitor is comprised of a wrist device and a cable, which includes an upper arm module and a chest module as shown in FIG. 1. The wrist device, upper arm module, and chest module each contain a three-axis accelerometer. In addition to the more traditional vital signs, the three accelerometers in the monitor capture data that can be used to estimate a patient's posture, the time spent in a specific posture, detect when a patient has fallen, and determine when the patient is walking.

The algorithm used to classify the life-threatening arrhythmias and atrial fibrillation can be provided on integrated circuitry within the chest module to measure and digitize ECG signals. The embedded software used to implement the algorithm is executed on a microprocessor located in the chest module.

Figure 2:
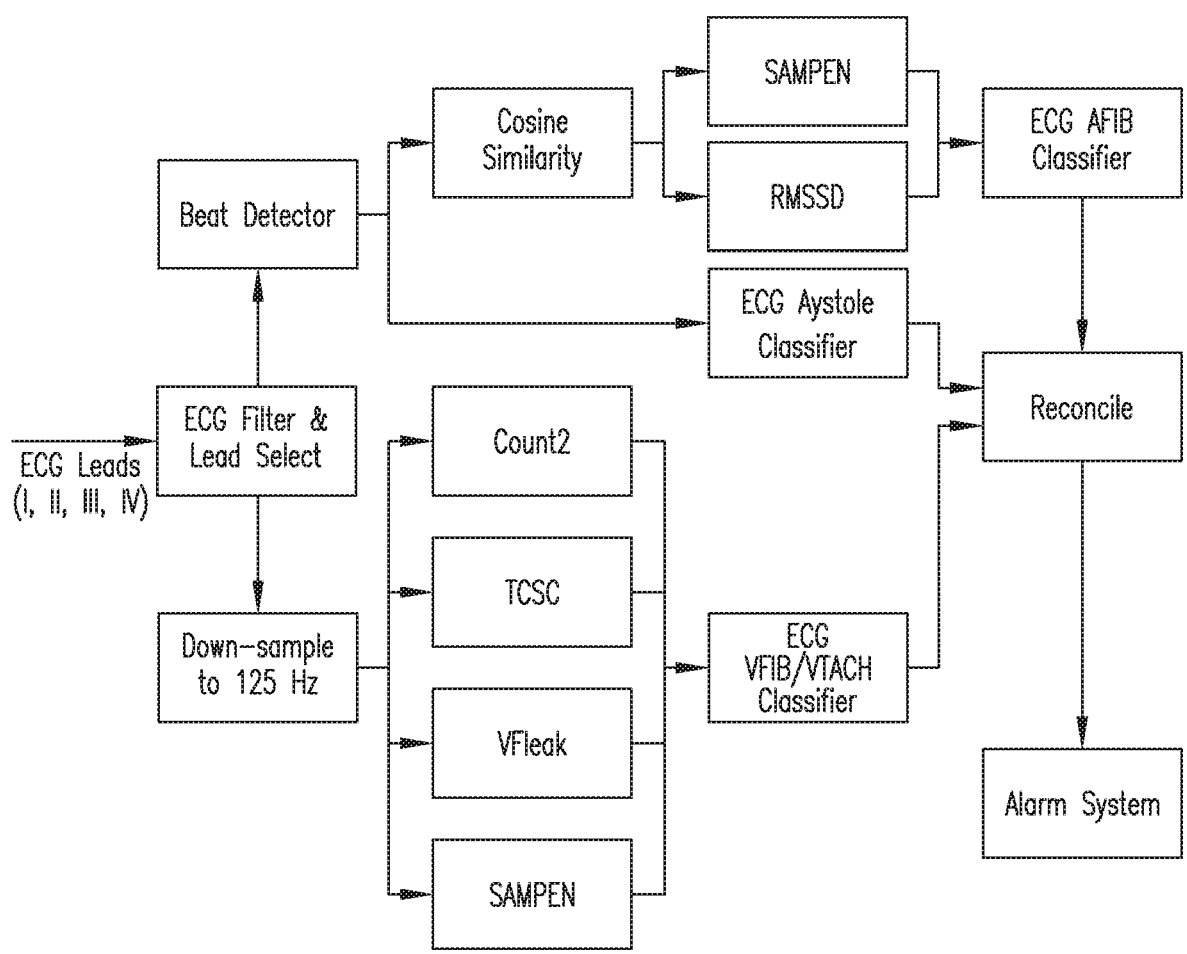
FIG. 2 depicts a block diagram of the asystole/atrial fibrillation monitoring system of the present invention.

A block diagram of the asystole/atrial fibrillation monitoring system of the present invention is shown in FIG. 2. The following describes this system in more detail.

ECG Filter & Lead Select

Filter

ECG waveforms for a three-wire cable (leads I, II, & III) and a five-wire cable (leads I, II, III, & V) are transduced and digitized using a Texas Instruments ADS1298R. The waveforms are digitized using a 24-bit delta-sigma analog to digital converter. The gain setting on the amplifier of the ADS1298R is six. The lowest significant bit in the digitized waveform is equivalent to 0.04768 microvolts. The ECG beat-picker and LTA+AF algorithms have some pre-defined thresholds that are sensitive to the scale of the waveform and any changes to the definition of the LSB would need to be propagated to these thresholds.

All available leads are sampled at a rate of 500 Hz and a digital filter is applied to them prior to their use by the ECG beat-picker and LTA+AF algorithms. The digital filter is a comb filter that provides a high pass −3 dB cut-off frequency of 0.5 Hz and has notch filters at multiples of 60 Hz.

Lead Select

ECG signal noise due to lead movement or muscle artifact may corrupt a single ECG lead or multiple ECG leads simultaneously. A challenge for a multi-lead ECG system is to develop an algorithm to combine or arbitrate between information from the different leads to improve the accuracy of any vital sign or event classification derived from these signals. Although kurtosis has been described in literature as a useful metric to distinguish between ECG signals with and without noise, the present invention utilizes a unique implementation in which this statistical metric is used to combine or exclude ECG leads from the ECG QRS detection algorithm used for heart rate calculation and AF classification.

Figure 4:
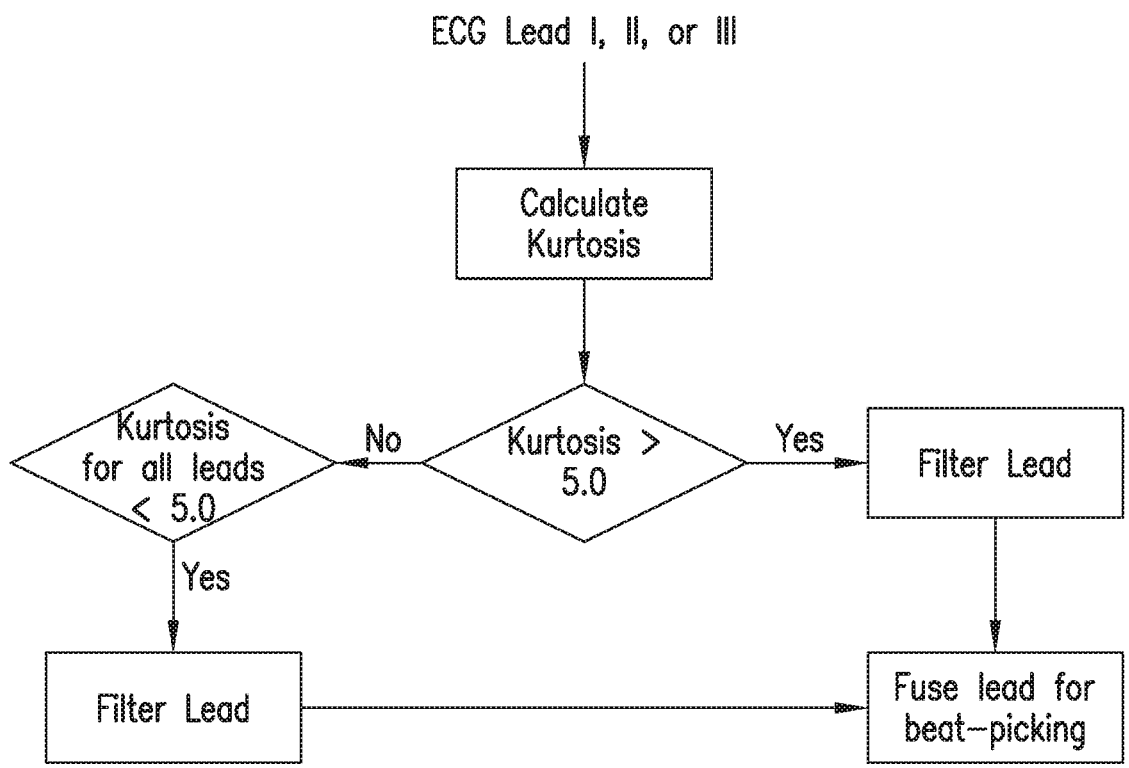
FIG. 4 depicts a flow diagram for an exemplary Lead Select algorithm.

A flow chart for the Lead Select algorithm is depicted in FIG. 4. The ECG beat-picker and atrial fibrillation algorithm utilize leads I, II, and III or any combination of those leads. An algorithm was developed to classify the quality of these three leads and automatically select a single lead or combination of the leads based on their signal quality.

The signal quality of an ECG lead is determined using a statistical measure of the signal known as kurtosis. The kurtosis of each ECG lead is calculated from a windowed ECG signal 8.192 seconds in length or using 4096 samples. The kurtosis of each lead is updated every 4 seconds. The equation given in (1) shows the kurtosis calculation for ECG lead k, where N=4096 ECG samples $y_k$, in the buffer with a mean signal value, $\bar{y}_k$. This calculation is performed for leads, k=I, II, III.

$$kurtosis_k[i] = \frac{\frac{1}{N}\sum_{i-N+1}^{i}(y_k[i]-\bar{y}_k)^4}{\left(\frac{1}{N}\sum_{i-N+1}^{i}(y_k[i]-\bar{y}_k)^2\right)^2} \quad (1)$$

Figure 3:
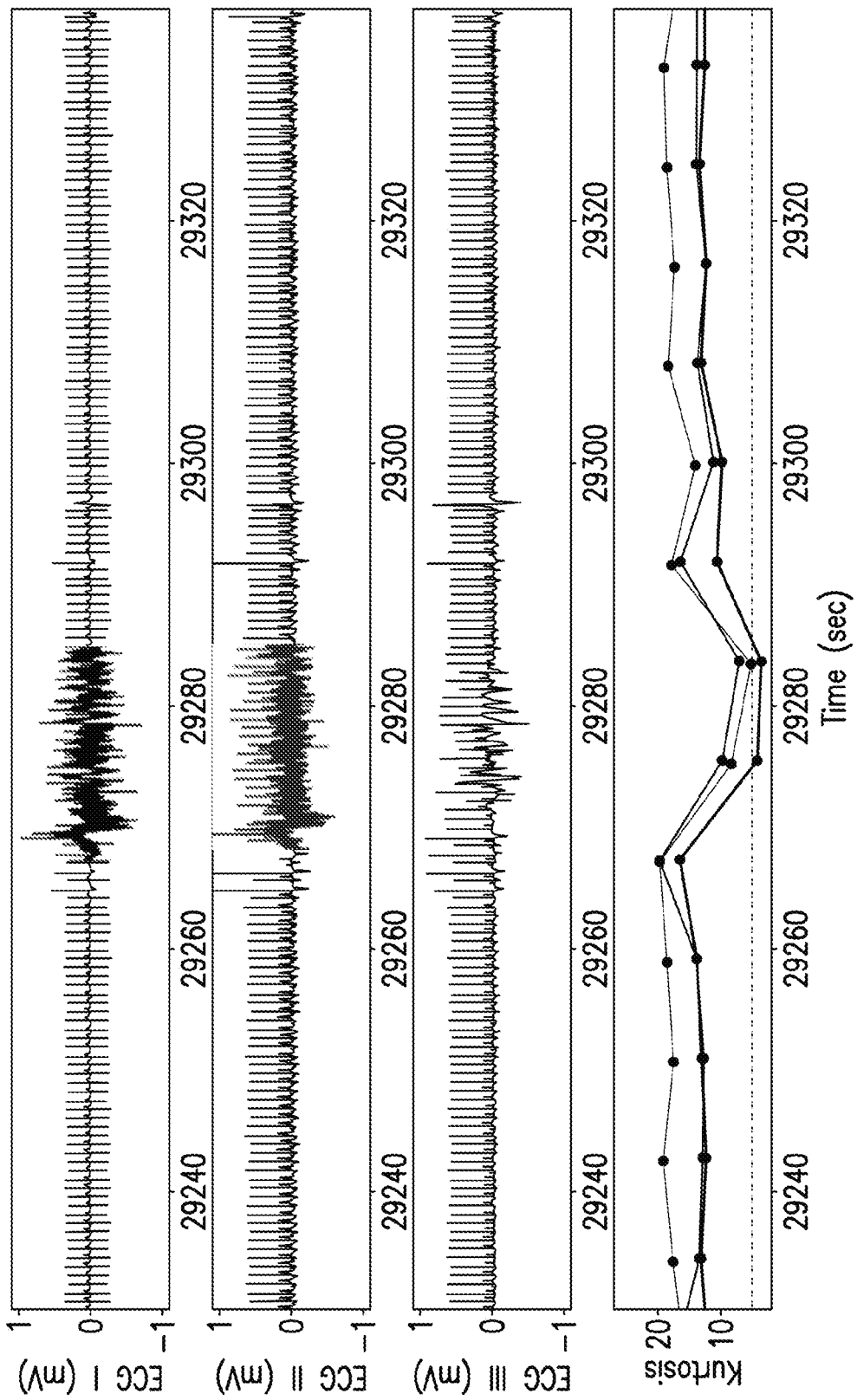
FIG. 3 depicts an exemplary plot of ECG lead signals and their corresponding kurtosis values.

A fixed threshold is used to evaluate the quality of each lead using the calculated kurtosis. If the kurtosis is above the threshold that lead is processed through a filter chain and fused with any other leads that are also above threshold. The fused waveform is then used by the beat-picker and feature extraction algorithms to classify atrial fibrillation. If all of the leads fall below the fixed threshold (e.g. 5) then all of the leads are accepted, processed through the filter chain, and fused for use by the ECG beat-picker and for feature extraction. A sample plot of ECG leads and their corresponding kurtosis values are shown in FIG. 3.

Similarly, the ventricular tachycardia and ventricular fibrillation algorithm may also utilize the kurtosis metric to select the appropriate leads for feature extraction and classification. The VTACH/VFIB algorithm extracts features from two ECG leads for classification. The leads are evaluated in order of preference V, II, I, and III depending on their availability. If the kurtosis of the lead is above the threshold it is used to generate features for the classifier. If the kurtosis of all of the leads are below the threshold then the two leads are selected in the order of preference depending on their availability.

ECG Beat Detector

Fiducial point selection of the QRS complex is critical for the time-dependent measurement of cNIBP. Electrode preparation, placement, electrical conduction, and cardiac axis all affect the QRS complex morphology. A change in any of these would cause errors in the temporal measurement of the QRS.

Pan-Tompkins processing is used to detect the full width of the QRS complex without distortion from changes in the Q, R or S waves. Out of band noise is filtered out and does not distort the signal. Stable fiducial points on this peak are used for the cNIBP timing measurement.

The Gravity Cliff Detector is designed to reject in-band noise by selecting its parameters based on performance on challenging annotated datasets. The look-behind style of beat detection permits all temporal information to be available at the time of the detection decision, which removes the need to carefully manage the internal states of the detector.

Pan-Tompkins (PT) Signal Processing

A 5 to 15 Hz bandpass filter is applied to each signal, to select frequencies common to the QRS complex.

6-pole Butterworth band-pass filter

Cascaded set of three different 2-pole filters

Designed in floating point, scaled to use integer coefficients 29 sample delay

A five-point derivative filter is applied to each signal, to accentuate rapid changes in voltage, common in the QR and RS segments.

$$y(t)=\frac{1}{64}[x(t)+16 \cdot x(t-4)-16 \cdot x(t-12)-x(t-16)]$$

8 sample delay

A squaring stage is applied to each signal, to magnify large values and rectify negative values.

$$y(t)=[x(t)]^2$$

No delay

A moving window sums each signal, creating peaks where QRS complexes exist amongst a low noise floor.

$$y(t)=\sum_{n=0}^{75}x(t-n)$$

38 sample delay

Valid leads are on the patient and have a kurtosis above a threshold. Processed signals from valid leads are averaged to create a single signal. This signal is always positive, and QRS complexes appear as peaks.

Gravity Cliff Detection (GCD)

The beat detection algorithm identifies beats on their falling edge rather than on their rising edge as is standard practice for traditional beat picking algorithms. This technique allows interrogation of the entire beat prior to its classification as a beat reducing the false positive rate.

The GCD picker is applied to the fused signal after being processed through the Pan-Tompkins filter chain. The GCD simulates constant negative acceleration on a particle that is moving with time along the signal. The magnitude of the signal is interpreted as a height value. When the particle drops below the signal height, the position is set to the signal height and the velocity is set to zero, akin to hitting the ground.

Figure 5:
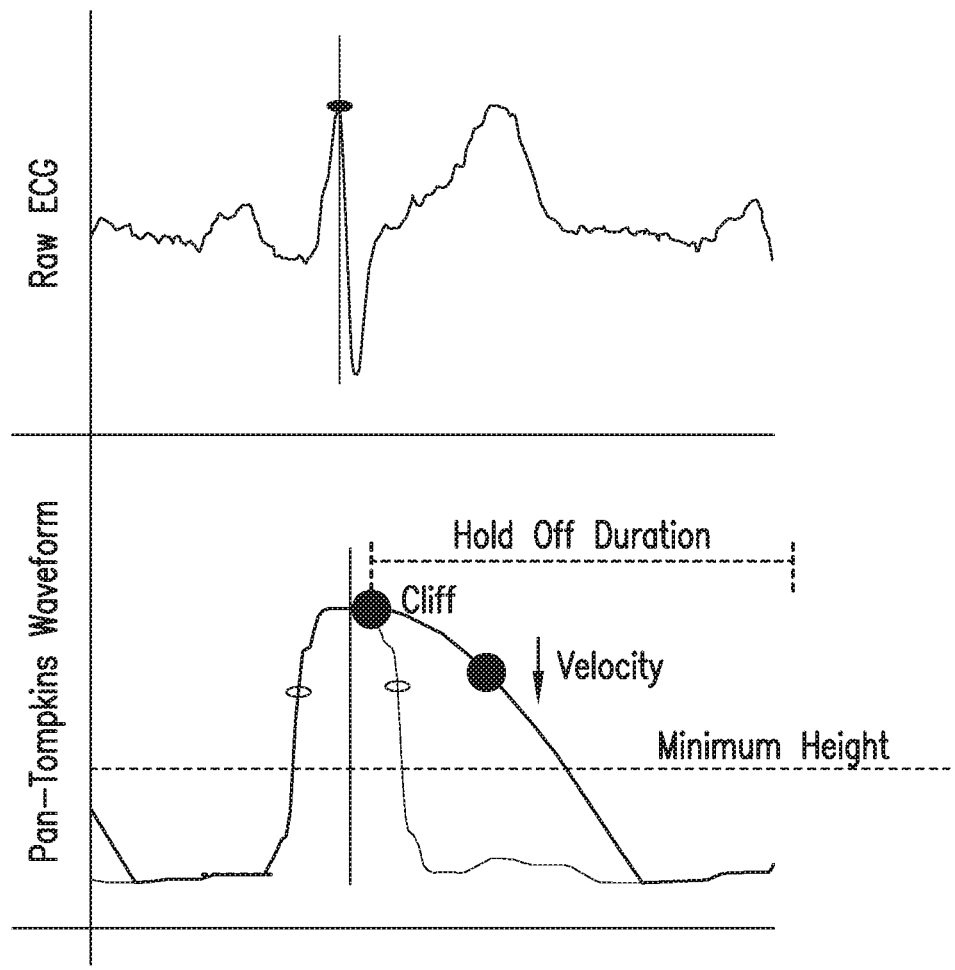
FIG. 5 depicts a raw ECG waveform and a corresponding Pan-Tompkins waveform which demonstrates a GCD picker being applied in graphical form.

As the particle falls off the top of a peak in the signal, it accelerates towards the signal baseline and its velocity increases analogous to a freefall. The particle position also moves closer to the amplitude of the current signal. While in this freefall state if the velocity exceeds a threshold then a cliff is detected at the time and amplitude value of the signal at the start of the free fall period. Prior to being selected as a beat the candidate cliff point must meet several criteria outlined below.

cliff amplitude>minimum cliff height duration since the last valid cliff>hold off duration If the signal amplitude at the point of detection meets these criteria it is considered a valid beat and the particle is reset to the current signal height with a velocity of 0. The relevant variables and thresholds for the GCD are shown in FIG. 5.

Asystole

The Asystole determination relies on the ECG beat detector. If a normal or ventricular beat is not detected for a specified period of time the monitor will alarm on Asystole. The period of time is user configurable between 4-15 seconds.

The ViSi Mobile monitor can measure heart rate from both the ECG and pulse rate from the optical sensor at the base of the thumb. This allows the device to mitigate false Asystole calls on the ECG using pulse rate. The monitor will alarm on Asystole if a normal or ventricular beat is not detected for a specified period of time and if there is not a valid, current pulse rate available. Pulse rate is determined as the median pulse interval in a 15-second moving window. Pulse intervals are calculated as the time difference between fiducial points on successive beats detected in the photoplethysmogram (PPG) signal. The pulse rate algorithm updates pulse rate every 3 seconds. If the number of PPG beats in the 15-second window drops below a minimum of 3 beats, pulse rate will not display a valid value and it will not suppress an Asystole alarm.

Atrial Fibrillation

The alarms for atrial fibrillation may be divided into two categories: 1) atrial fibrillation with rapid ventricular response (AFIB RVR) and 2) atrial fibrillation with controlled ventricular response (AFIB CVR). The algorithm used to classify atrial fibrillation is the same for both alarms they are differentiated only by the patient's current heart rate.

The RR intervals measured by the ECG beat detector are the primary input to the atrial fibrillation classifier. For every ECG beat detected an RR interval is determined as the time difference between the fiducial point marking the current beat ($t_k$) and the fiducial point marking the previous beat ($t_{k-1}$). The fiducial points for each ECG beat are determined as the midpoint of the integrated Pan-Tompkins waveform.

Cosine Similarity

Increased RR interval variability can be caused by atrial fibrillation, the presence of ventricular escape beats, and erroneous beat-picks due to signal artifact. The morphology of adjacent beats can be compared and used to identify intervals that were derived between ventricular beats, normal beats, and signal artifact. Unwanted RR intervals can be excluded from the atrial fibrillation classifier to prevent false positive event classifications.

Figure 9:
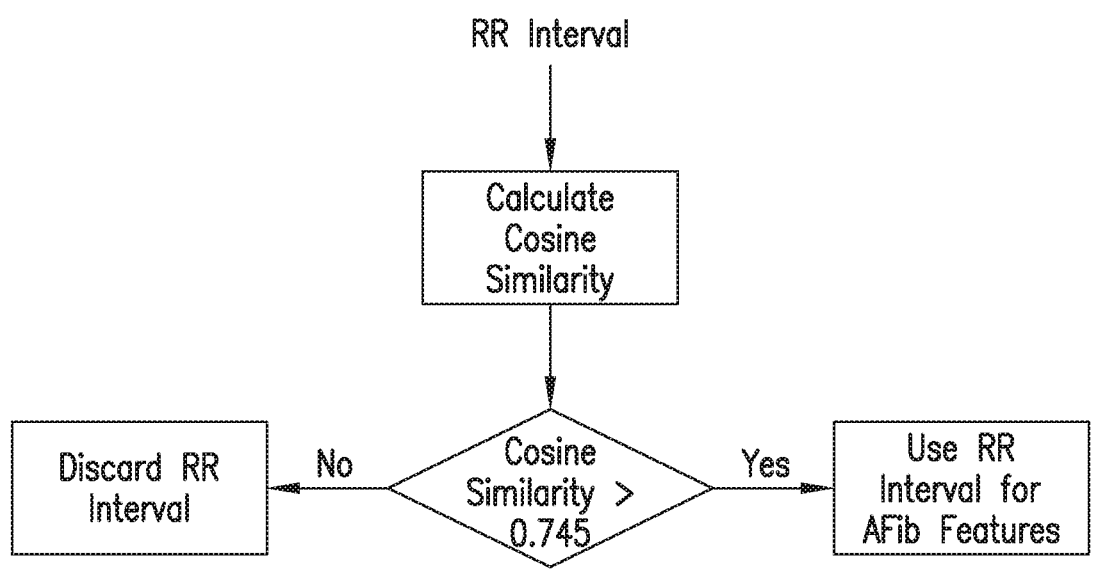
FIG. 9 depicts a flow diagram for an exemplary RR interval screening algorithm.

A flow diagram for RR interval screening is shown in FIG. 9. The method used to compare adjacent beat morphology begins with the ECG beat-picker that identifies beats and determines a fiducial point on the signal that is processed through the Pan-Tomkins filter chain.

The second stage of the method performs a comparison of the unfiltered ECG signal before and after the fiducial points on the adjacent beats. A cosine similarity metric is used to compare ECG waveform segments surrounding the two fiducial points one which occurred at sample time j and the other at sample time k and then used to calculate the RR interval (RR=k−j). The formula for cosine similarity is given in (2) where y[i] is the unfiltered ECG signal from a single lead and N=20 is the number of samples included before and after the fiducial point.

$$\text{similarity} = \frac{\sum_{i=-N}^{N} y[j+i]y[k+i]}{\sqrt{\sum_{i=-N}^{N} (y[j+i])^2} \sqrt{\sum_{i=-N}^{N} (y[k+i])^2}} \quad (2)$$

Figure 6:
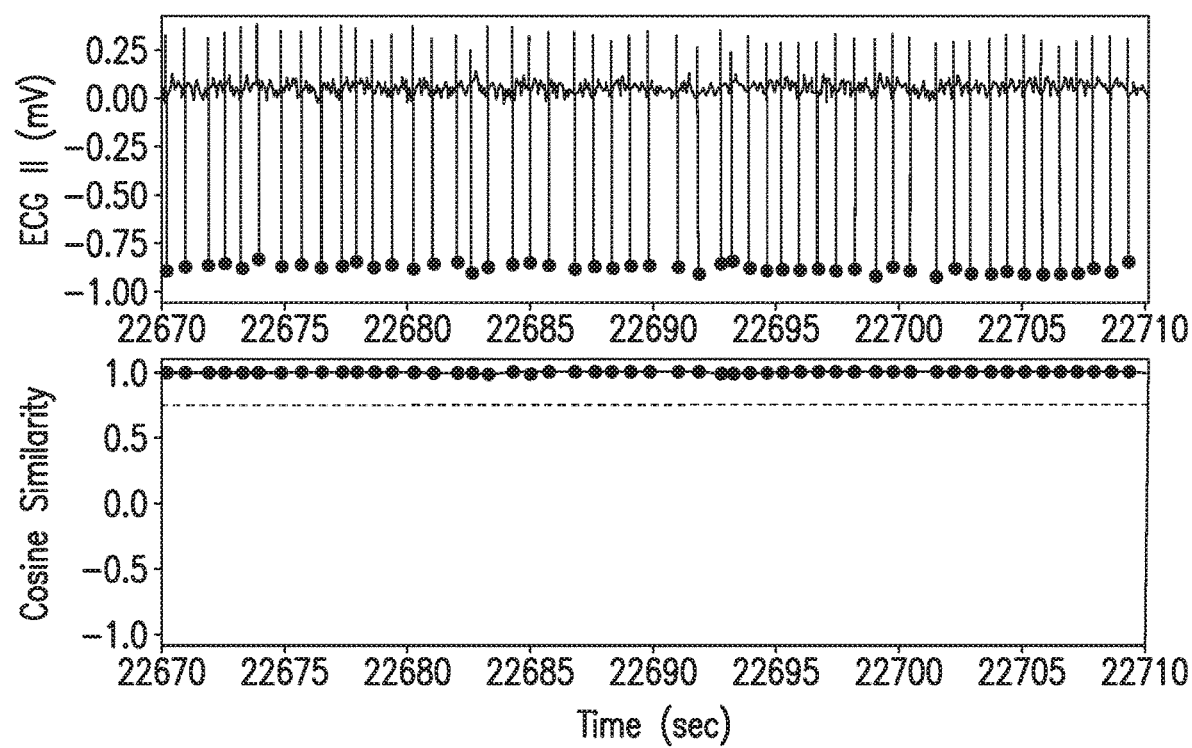
FIG. 6 depicts RR interval variability in an ECG signal and a corresponding cosine similarity analysis of the ECG signal in a patient with atrial fibrillation.
Figure 7:
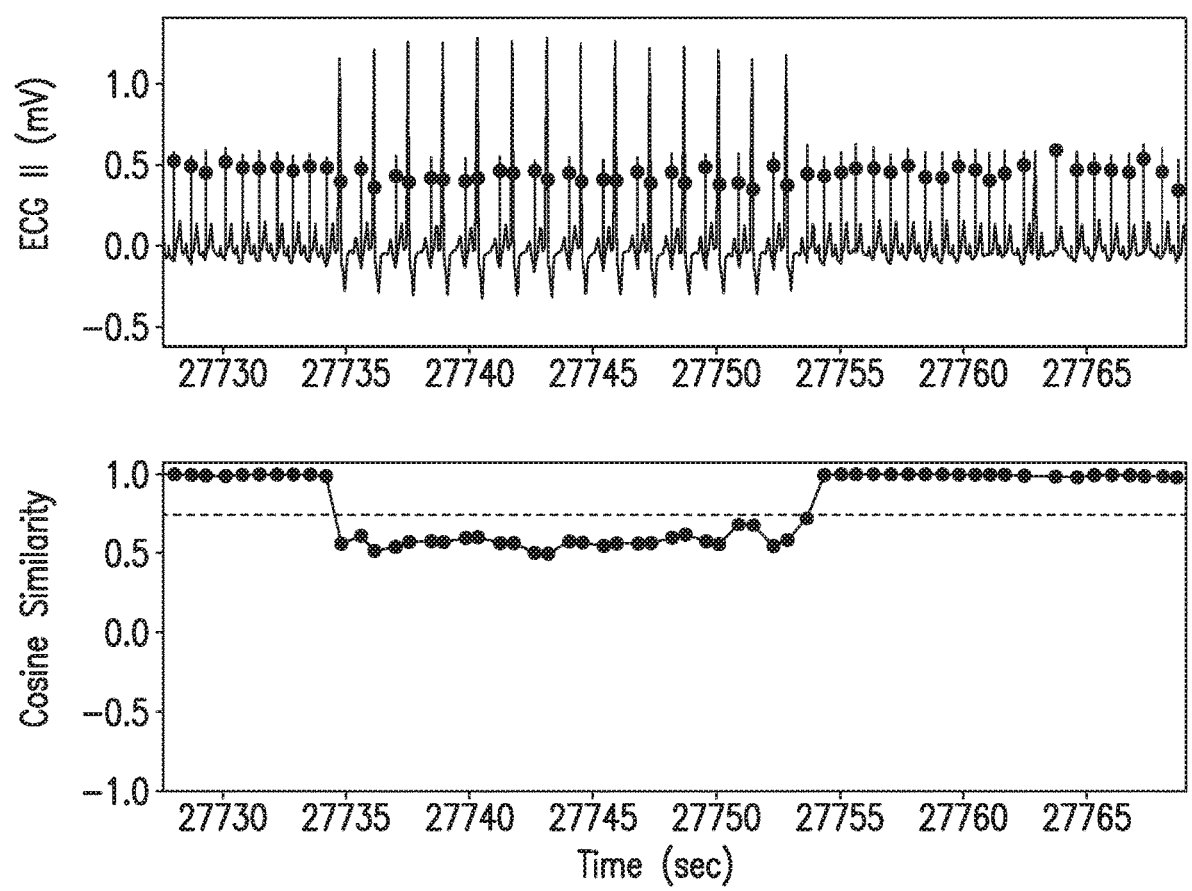
FIG. 7 depicts RR interval variability in an ECG signal and a corresponding cosine similarity analysis of the ECG signal in a normal subject.
Figure 8:
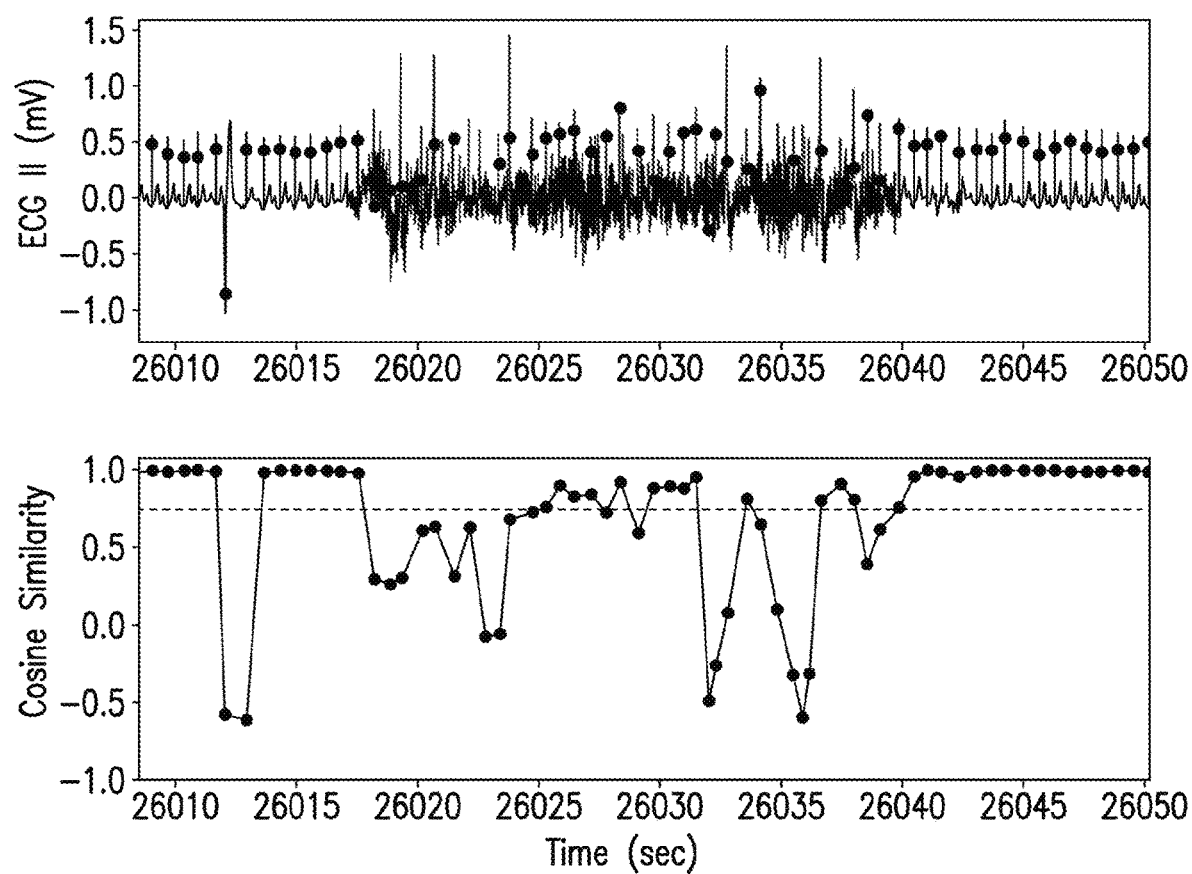
FIG. 8 depicts an analysis as described for FIGS. 6 and 7, but applied to false beats due to signal artifacts.

FIG. 6 shows a cosine similarity analysis of an ECG lead trace for a patient with atrial fibrillation; FIG. 7 shows a similar analysis for a patient exhibiting normal and ventricular beats; and FIG. 8 shows a similar analysis of false beats due to signal artifacts. If the cosine similarity metric is above a pre-specified threshold (e.g. 0.745) the AFIB classifier uses the RR interval, if it is below the threshold it is excluded from being used to calculate the two features. The AFIB classifier is updated every 30 seconds. The classifier uses a 136 second moving average window. The 90 most recent RR intervals are used to generate the features in the classifier. If 60 acceptable RR intervals are not contained in the 136-second window the algorithm will not update the AFIB classification.

SAMPEN & RMSSD

Figure 10:
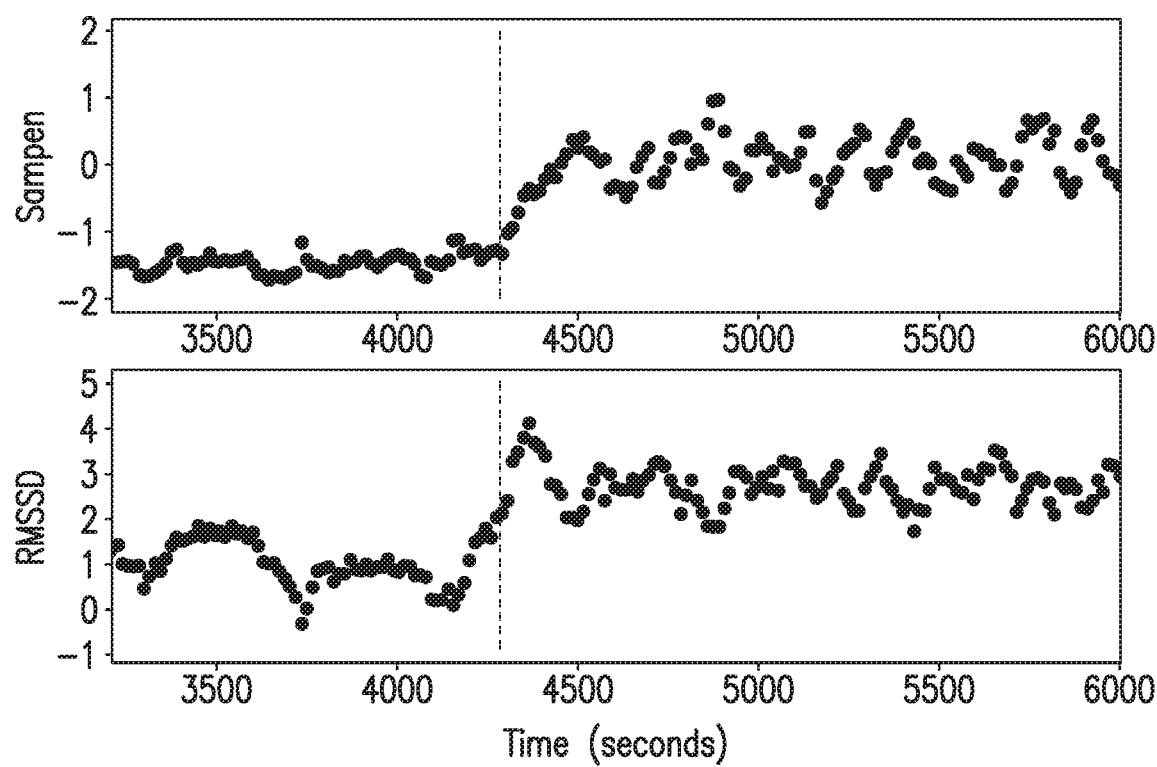
FIG. 10 depicts an exemplary SAMPEN and RMSSD before and after the onset of AFIB.

The classification method uses two features to classify AFIB. The first feature RMSSD is the root mean square of successive differences in RR intervals. The second feature SAMPEN is the sample entropy of the successive differences in RR intervals. FIG. 10 shows an exemplary SAMPEN and RMSSD before and after the onset of AFIB (onset indicated by the dashed line).

ECG AFIB Classifier

The machine learning classifier used to determine AFIB in this two-dimensional feature space is based on a geometric approximation of the classification regions described by a support vector machine classifier trained on annotated ECG data. The support vector machine utilized radial basis function kernels and was not computationally efficient enough to be implemented into the embedded software. Therefore, multiple circles and arcs were used to approximate the AFIB classification region and allow a simplified embedded implementation. If the features described a point located within the classification region the model classified the features as AFIB. If they describe a point outside of the classification region the model classified the features as Not AFIB.

Figure 11:
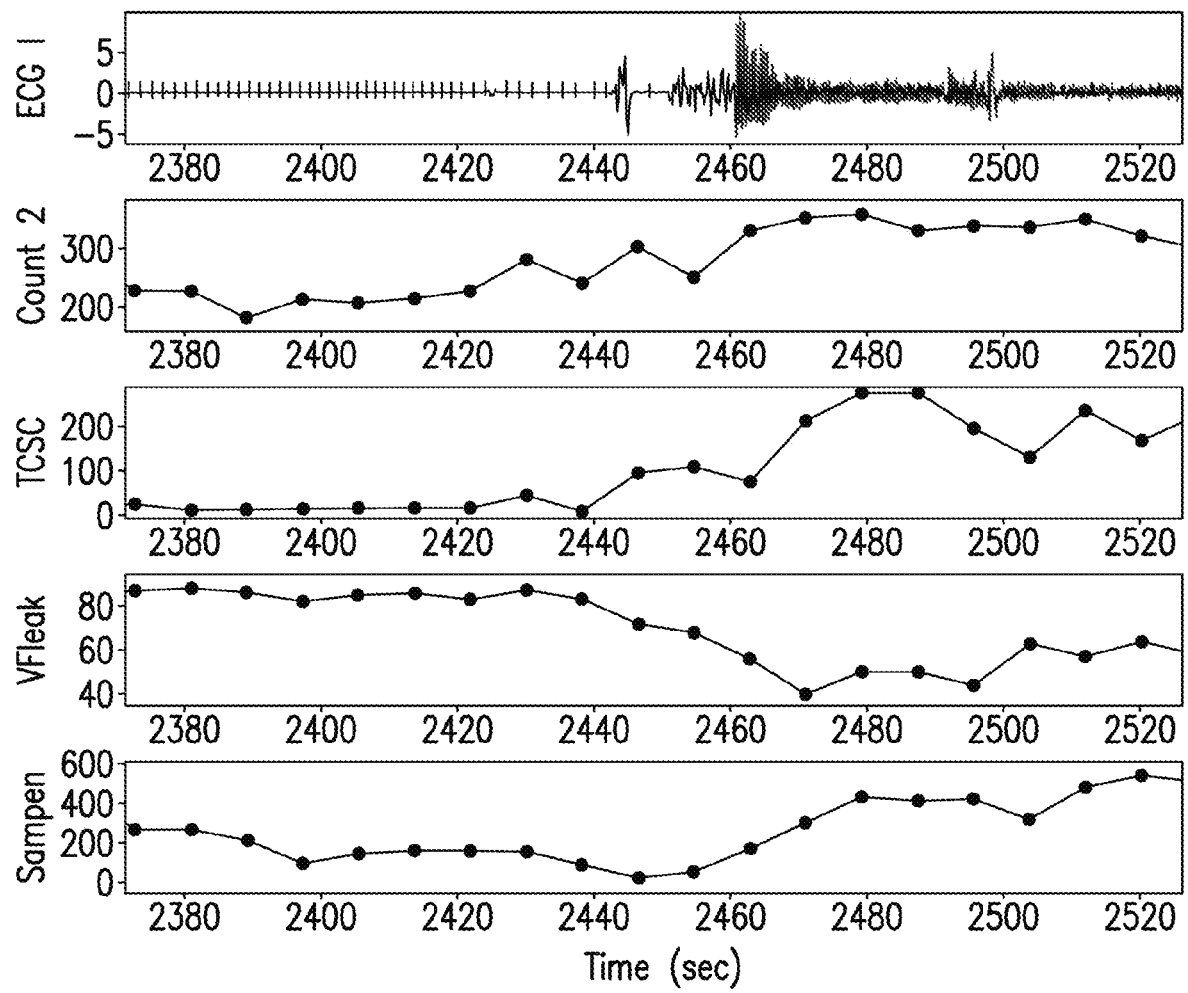
FIG. 11 depicts an exemplary time series of ECG trace, Count 2, TCSC, VFleak, and Sample entropy before and after a VFIB/VTACH event.

FIG. 11 shows an exemplary time series of ECG trace, Count 2, TCSC, VFleak, and Sample entropy before and after a VFIB/VTACH event. An AFIB alert is triggered when AFIB is classified for two consecutive updates. The type of AFIB message that is displayed depends on the patient's heart rate. If the Heart rate is above the user-defined value, then the device alerts with the message "AFIB-RVR" for rapid ventricular response. If the patient's heart rate is below the user-defined value the device alerts with the message "AFIB-CVR" for controlled ventricular response.

The heart rate algorithm utilizes a 20 second moving window to determine heart rate. The heart rate algorithm updates heart rate at 1-second intervals. For every ECG beat detected an RR interval is determined as the time difference between the fiducial point marking the current beat and the fiducial point marking the previous beat. The heart rate is determined as the inverse of the average RR intervals of all of the ECG beats detected in the 20-second window. If an ECG beat is not detected in the last 3 seconds prior to the time of the current HR update an additional RR interval is added to the sum used to determine the average interval. The additional RR interval is calculated as the time difference between the update time and the last ECG beat detected. If no ECG beats are detected in the 20-second interval the heart rate is set equal to 0.

Ventricular Tachycardia and Ventricular Fibrillation

A set of 4 features derived from the ECG waveform is used to classify rapid ventricular tachycardia (VTACH) and ventricular fibrillation (VFIB). The classifier does not distinguish between the two different life-threatening arrhythmias and generates a single alarm to alert in the event that either of them is detected ("VTACH/VFIB").

The inputs to the VFIB/VTACH algorithm are non-overlapping windowed segments of the filtered ECG waveform. The windows are 8.192 seconds in duration. Prior to windowing the data, the ECG waveform was down-sampled from 500 Hz to 125 Hz in order to maximize efficiency and minimize the memory required to generate the features. Each windowed data segment consists of 1024 ECG samples.

Count2, TCSC, VFleak, and Sample Entropy

The method generates four features from each windowed ECG data segment. These features are used as inputs into the machine learning classifier used to detect VFIB/VTACH. The four features are Count 2, TCSC, VFleak, and sample entropy.

The method also finds the minimum and maximum value of the signal over each window. At the end of each window the difference between the maximum and minimum values are taken. If the difference is less then 150 then a "flat-line" condition is flagged, and the lead will not be used for classification.

ECG/VFIB/VTACH Classifier

The method utilizes a machine learning classifier to determine VFIB/VTACH in a complex four-dimensional feature space that can be implemented on the constrained resources of a small, body worn, low-power, embedded system.

Figure 12:
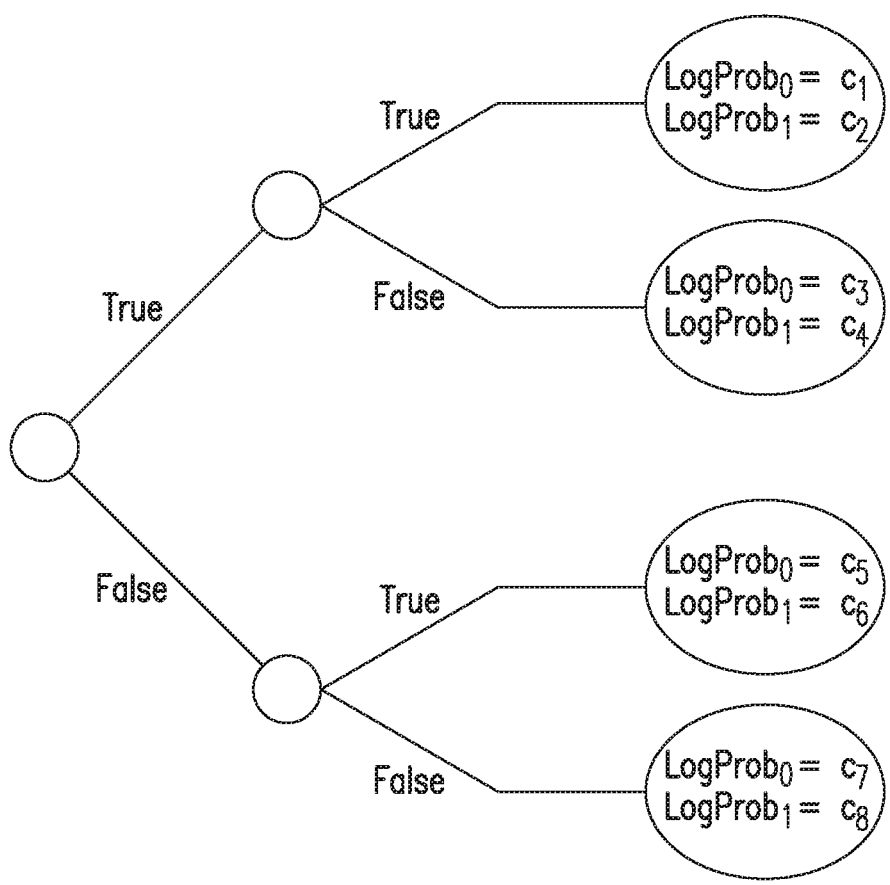
FIG. 12 depicts an exemplary adaptive boosting tree (AdaBoost) machine learning classifier for application to identify a VFIB/VTACH patient event.

An adaptive boosting tree (AdaBoost) machine learning classifier was developed to determine if the four features indicate a VFIB/VTACH patient event. The classifier employs 163 decision trees each having a maximum depth of two decision nodes. Each leaf of the tree provides a logarithmic probability for both of the possible classifications (0 or 1) as shown in FIG. 12, where the circles indicate the decision nodes which can operate on any one of the 4 features and the ovals are the unique logarithmic probabilities for each leaf.

The output of the classifier LogProbSum for a single ECG lead is the weighted sum of the log probabilities from each decision tree i, for both classes as shown in (3a) and (3b). The output of each tree is multiplied by a unique weight, $w_i$.

$$LogProbSum_0 = \sum_{i=0}^{162} w_i \times LogProb_0[i] \quad (3a)$$

$$LogProbSum_1 = \sum_{i=0}^{162} w_i \times LogProb_1[i] \quad (3b)$$

The probability $P_1$ that a VFIB/VTACH event has occurred is determined using the equation in (4)

$$P_1 = \frac{\exp(LogProbSum_1)}{\exp(LogProbSum_0) + \exp(LogProbSum_1)} \quad (4)$$

Four features are simultaneously calculated on two independent ECG leads. The features generated from each lead allow the AdaBoost classifier to generate a unique probability for each lead every 8.192-second window. The two leads used by the algorithm to generate the features depend on the available leads for a three or five wire cable. The priority of the two leads used by the algorithm is provided below in ranked order: (1) Lead V, (2) Lead II, (3) Lead I, and (4) Lead III. This priority was determined based on an analysis of sensitivity and specificity on annotated patient data.

Figure 13:
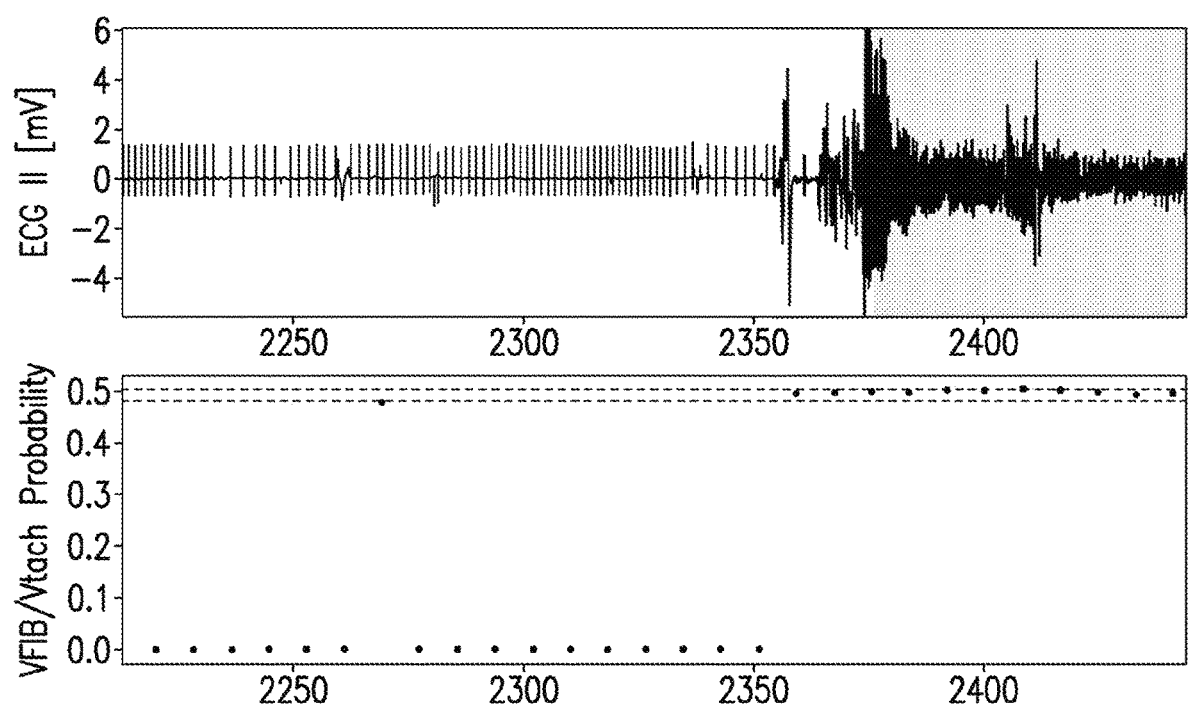
FIG. 13 depicts an exemplary time series of probabilities generated by the AdaBoost classifier before and after a VFIB/VTACH event.

An exemplary time series of probabilities generated by the AdaBoost classifier before and after a VFIB/VTACH event is shown in FIG. 13. The VFIB/VTACH alarm is triggered when the probability of VFIB/VTACH determined by the AdaBoost classifier for both leads surpass a pre-specified threshold for two consecutive windows. VFIB/VTACH alarm will be cancelled when both leads fall below a different pre-specified threshold for two consecutive windows.

Arrythmia Reconciliation

The LTA+AF classifiers for ECG are independent of each other and on rare occasions require some arbitration in terms of alert priority. Additionally, in some instances the arrhythmia classifications dictate whether heart rate or pulse rate are displayed on the PWD or RVD. The arrhythmia alerts are prioritized in the following order: (1) VFIB/VTACH, (2) Asystole, (3) AFIB-RVR/AFIB-CVR.

ECG Noise and Artifact Classifier

The AdaBoost VFIB/VTACH can be extended to include a classifier for noise or artifact. Using the same underlying feature set, the classifier can be trained to output probabilities for three possible classifications (VFIB/VTACH, Noise/Artifact, Other).

The Noise/Artifact probability can serve two roles within the system. First, to suppress heart rate calculation during periods of excessive artifact or noise; second, to provide additional information to the reconciliation step which can be fused with other modalities (as discussed below) to help distinguish between VFIB/VTACH and artifact that closely resembles VFIB/VTACH.

PPG/ECG Fusion

As a measure of pulsatile activity, the photoplethysmogram (PPG) provides another window into a patient's cardiac rhythms. Arrhythmias such as VTACH, VFIB, and AFIB not only alter the timing between pulses but also alter end diastolic volume leading to large variations in pre-ejection period and left ventricular ejection time, stroke volume, and pulse amplitude all detectable using the PPG and Pulse Arrival Time.

PPG/AFIB Classifier

A significant challenge for an AFIB classifier based on RR interval variability are the false positives generated when the ECG signal is corrupt by artifact. If the source of the artifact in the ECG signals is independent from artifact in the PPG signals, the PPG signal may provide a methodology to suppress false AFIB classifications. Additionally, when only the PPG signals are available the signals may be used to classify AFIB independently.

With some minor modification, the feature extraction methods that were applied to RR intervals in the ECG (SAMPEN & RMSSD) can also be applied to pulse intervals (PI) measured by the PPG for classification of Atrial Fibrillation. A region can be defined in the two-dimensional feature space derived from the pulse intervals to delineate AFIB from NON-AFIB using a variety of machine learning techniques such as an ensemble method like the AdaBoost algorithm or support vector machine using a variety of kernels to map the features to higher dimensions. If the ECG signals contain artifact that cause a false AFIB classification based on RR intervals and the PI intervals derived from PPG indicate that the patient is not in AFIB using a separate classifier the alarm could be suppressed or it could be delayed for a period of time.

Figure 14:
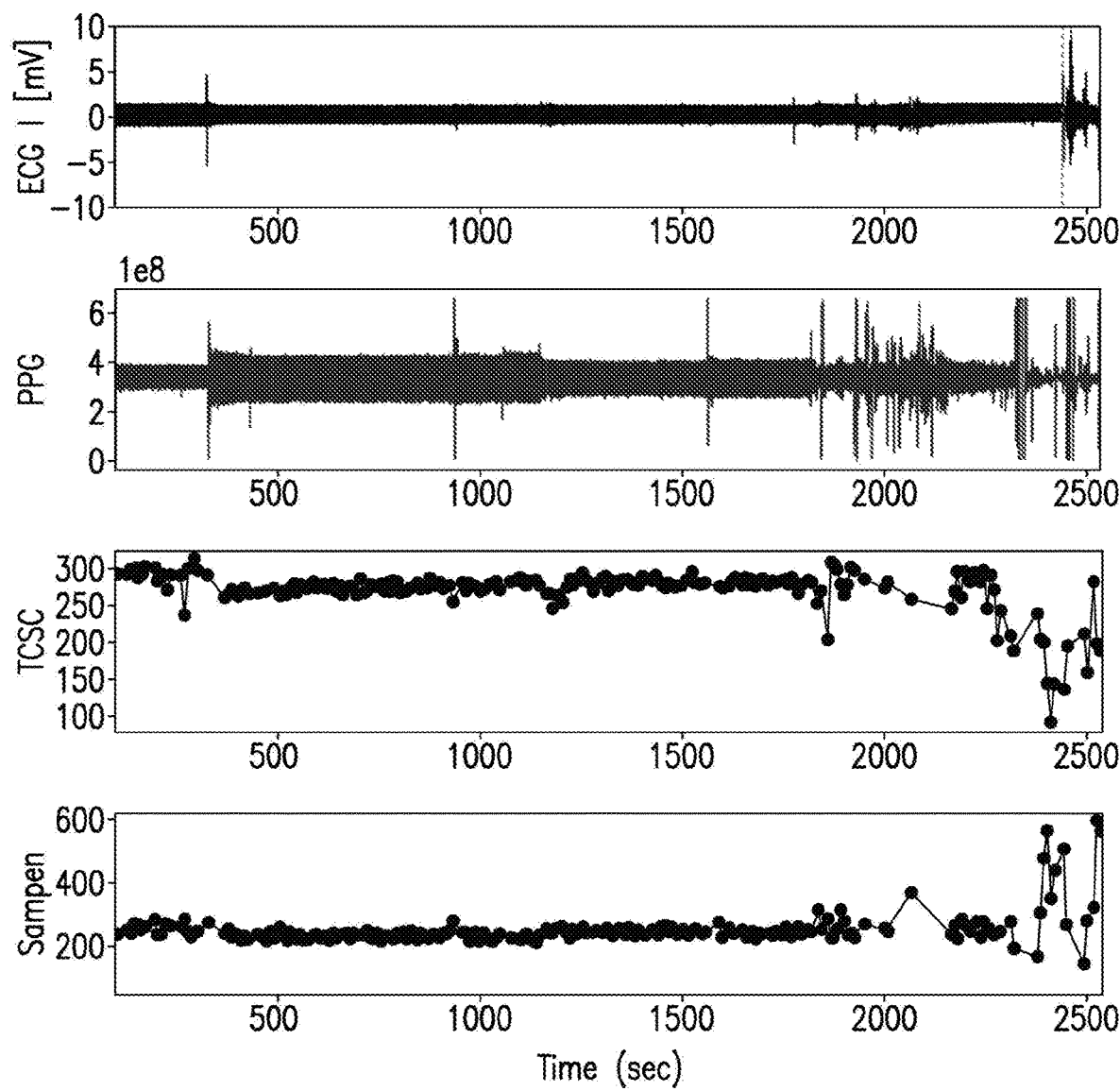
FIG. 14 depicts an exemplary time series of ECG, PPG, TCSC, and sample entropy being applied to distinguish normal sinus rhythm from other rhythms and artifact in the PPG.

Alternatively, the two PI based features $SAMPEN_{PI}$ & $RMSSD_{PI}$ derived from the PPG signals could be combined with the $SAMPEN_{RR}$ and $RMSSD_{RR}$ features derived from the RR intervals measured with the ECG signals to create a four-dimensional feature space that can be delineated into two regions AFIB and NON-AFIB and used for classification and to generate an AFIB alarm PPG/VFIB/VTACH Classifier A significant challenge for VFIB classification are the false positives generated when the ECG signal is corrupt by artifact. If the source of the artifact in the ECG signals is independent from artifact in the PPG signals, the PPG signal may provide a methodology to suppress false VFIB classifications. FIG. 14 shows an exemplary time series of ECG, PPG, TCSC, and sample entropy illustrate how these features can be used to distinguish normal sinus rhythm from other rhythms and artifact in the PPG. The dashed red line on ECG indicate the onset of a VFIB/VTACH event.

Figure 15:
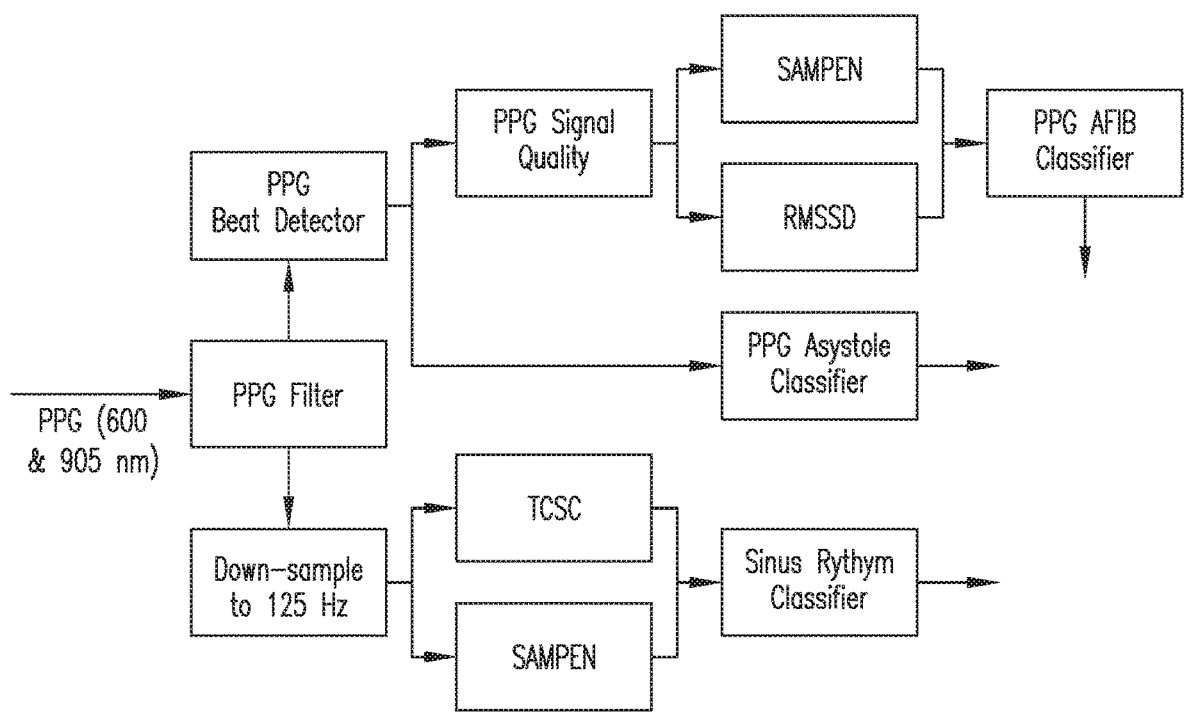
FIG. 15 depicts a flow diagram for an exemplary ventricular fibrillation event screening algorithm.

With some minor modification, two of the four feature extraction algorithms that were applied to the ECG signals (TCSC & SAMPEN) can also be applied to PPG signals for verification of a Ventricular Fibrillation event. FIG. 15 shows a flow diagram of such an implementation. A region can be defined in the two-dimensional feature space derived from the PPG signals to delineate sinus rhythm pulses from VFIB and other types of signal artifact using a variety of machine learning techniques such as an ensemble method like the AdaBoost algorithm or support vector machine using a variety of kernels to map the features to higher dimensions. If the ECG signals contain artifact that cause a false VFIB/VTACH classification and the PPG signal provides features (TCSC & SAMPEN) into a separate classifier to label the patient in normal sinus rhythm the annunciation of the alarm could be suppressed, be delayed for a period of time, or postponed for a series of consecutive VFIB/VTACH classifications from the ECG signals.

Accelerometer/ECG Fusion

As a measure of patient activity, the three accelerometers integrated into the ViSi Mobile monitor provide additional context to the VFIB, VTACH, and Asystole classifications. Knowledge of the type and level of patient activity can be used to extend the requirements on the number of consecutive classifications required to trigger an alarm or eliminate small time windows of data from being processed by the feature extraction algorithms. For example, an algorithm can be used to determine if significant changes in the features used to classify VFIB/VTACH and AFIB are correlated to changes in the patient's activity type or activity level.

Figure 16:
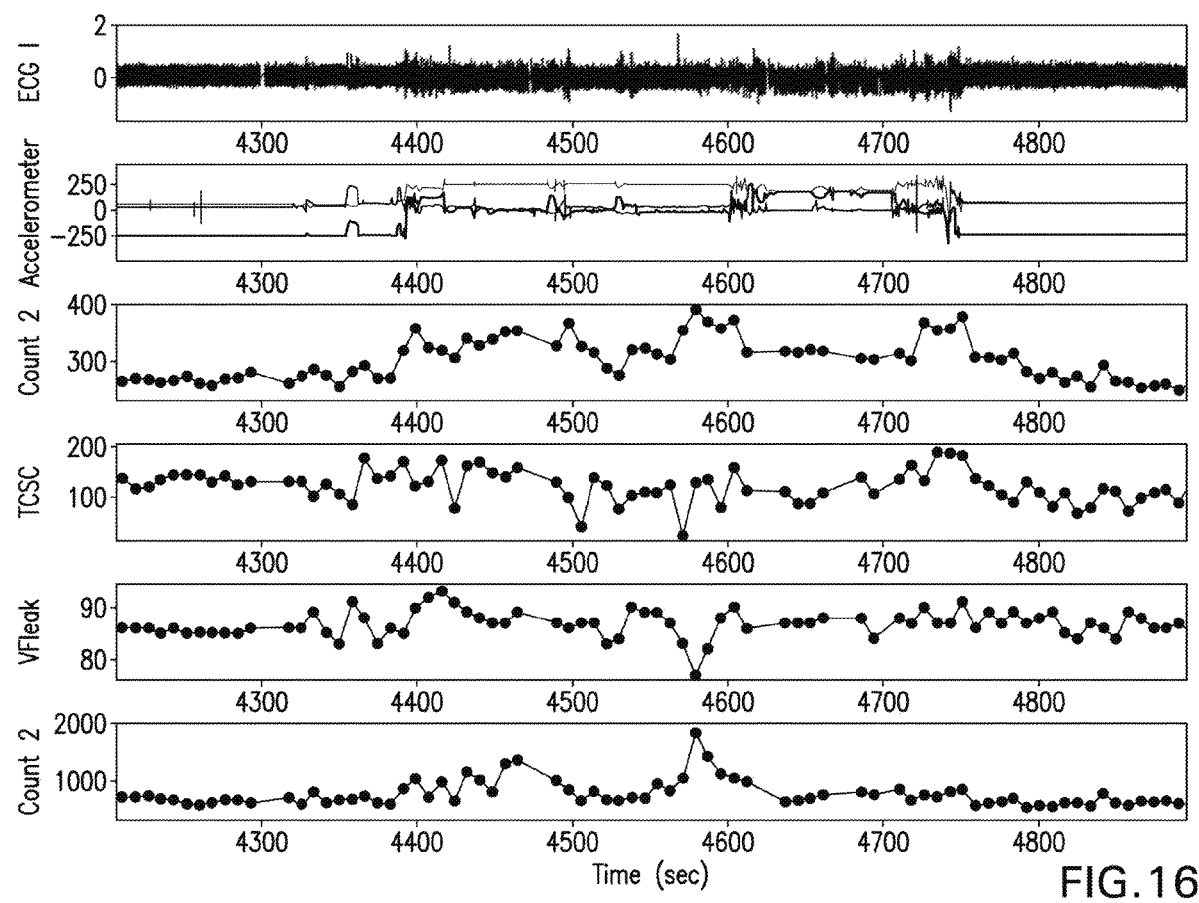
FIG. 16 depicts an exemplary time series of ECG, body worn accelerometer, and VFIB/VTACH features to illustrate their sensitivity to motion artifact caused by patient activity as measured by the accelerometer signals.
Figure 17:
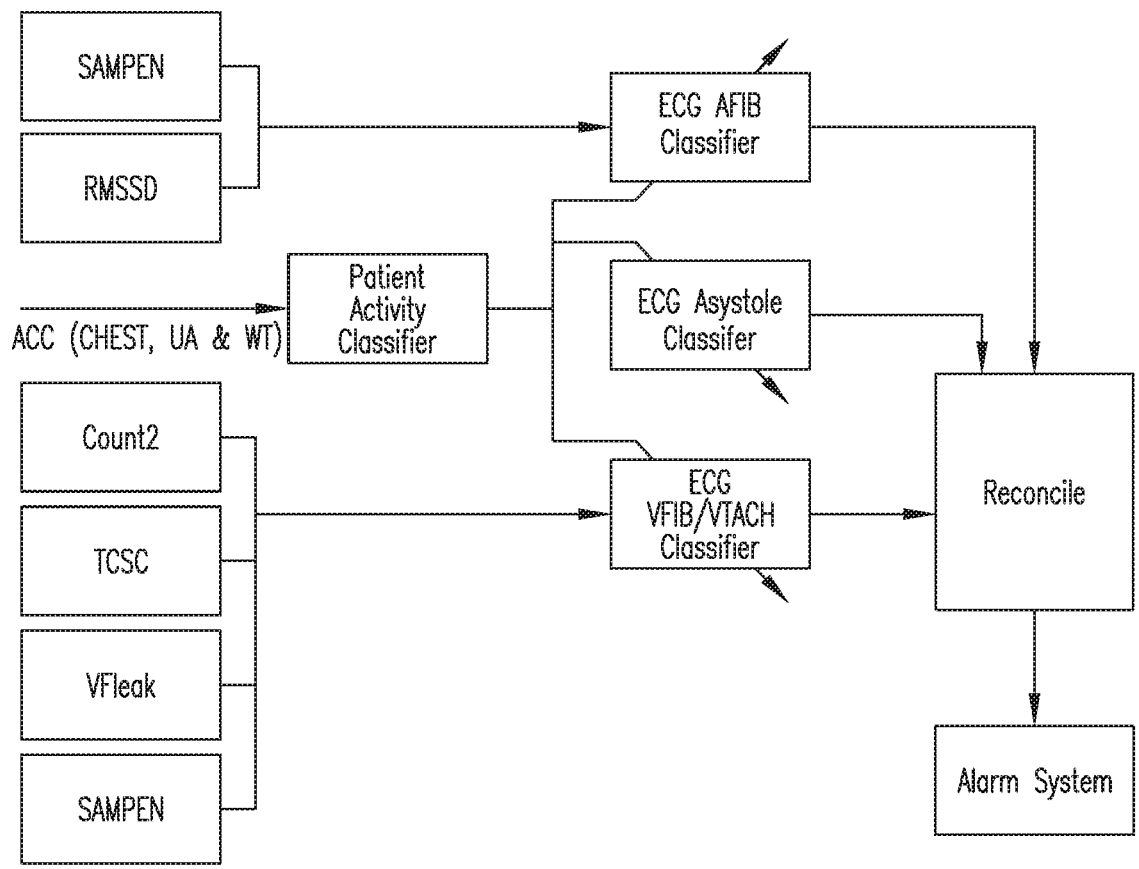
FIG. 17 depicts a flow diagram for an exemplary algorithm to correlate between activity and the predictive features indicative of false alarms, VFIB/VTACH and AFIB.
Figure 18:
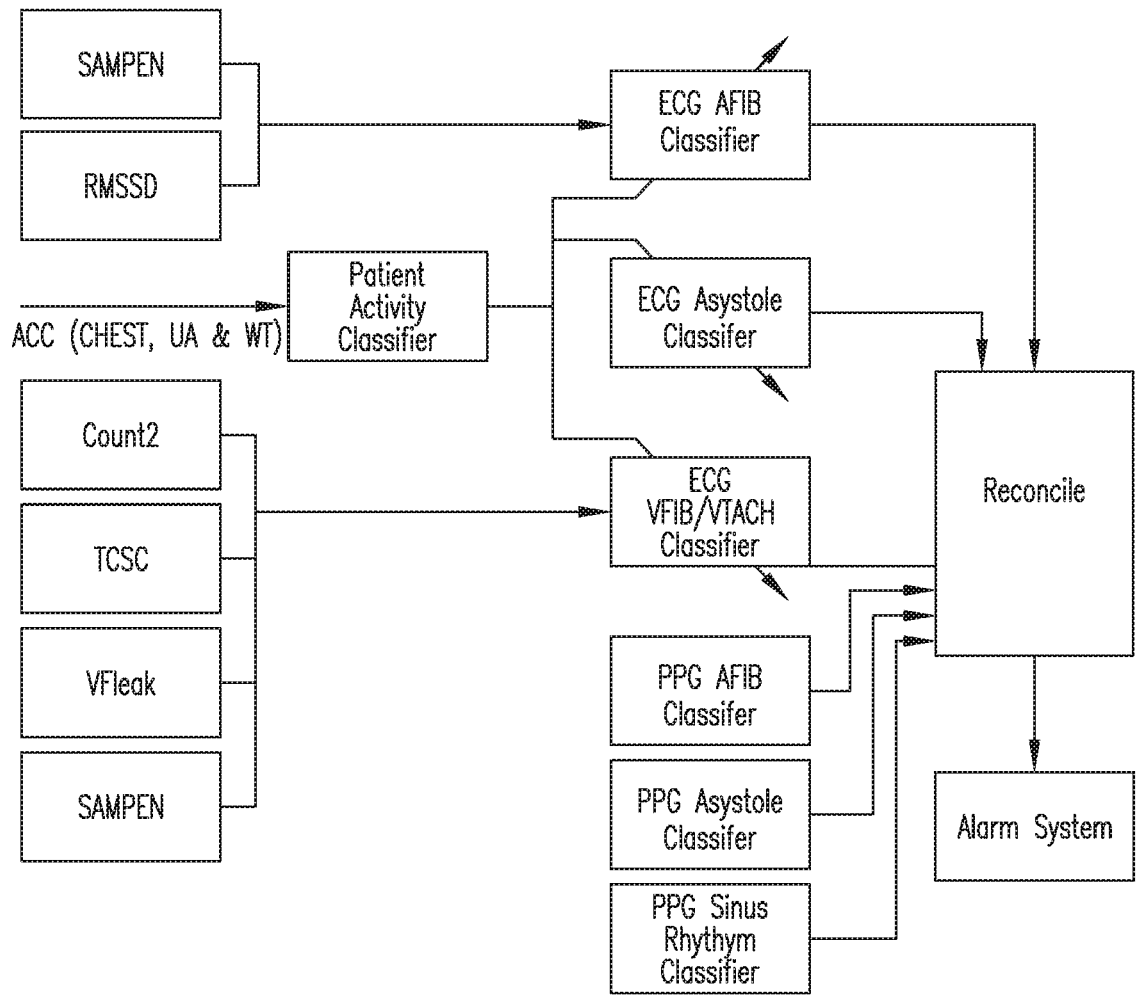
FIG. 18 depicts a flow diagram for fusion of PPG and ACC waveforms with ECG waveforms to identify LTA+AF.

FIG. 16 shows an exemplary Time series of ECG, body worn accelerometer, and VFIB/VTACH features illustrate their sensitivity to motion artifact caused by patient activity which is measured by the accelerometer signals. If VFIB/VTACH and AFIB signals are correlated to activity, the number of consecutive classifications required to alarm could be increased during these activity periods. Additionally, in the case of life threatening arrhythmias such as VFIB and Asystole, the ViSi Mobile system can self-annotate patient activities that cause false alarms based on resumption of a non-lethal rhythm following the alarm. This allows adaptive learning about the correlation between activity and the predictive features. A flow diagram of such a system is shown in FIG. 17. Similarly, Both the PPG and ACC can be fused with the ECG into the LTA+AF methods described herein as shown in FIG. 18.

The following are preferred embodiments of the invention.

Embodiment 1. A method for continuously monitoring a patient for cardiac electrical abnormalities, comprising:
obtaining a plurality of time-dependent electrocardiogram (ECG) waveforms from an ECG sensor comprising plurality of ECG electrodes, each waveform in the plurality of waveforms corresponding to electrical signals obtained from one ECG electrode in the plurality of ECG electrodes;
processing the plurality of waveforms by
   determining a time-dependent first signal quality parameter for each waveform in the plurality of waveforms and curating the plurality of waveforms by comparing each first signal quality parameter to a first quality threshold metric,
   wherein if at least one first signal quality parameter exceeds the first quality threshold metric, accepting those waveforms having a first signal quality parameter that exceed the first quality threshold metric and discarding those waveforms having a first signal quality parameter that does not exceed the first quality threshold metric, or if no first signal quality parameter exceeds the first quality threshold metric, accepting all waveforms, and
   combining the accepted waveforms to provide a time-dependent combined ECG waveform;
processing the combined ECG waveform to by
   identifying each QRS complex in the combined ECG waveform,
   determining a second signal quality parameter for each QRS complex by gravity cliff detection, and
   curating each second signal quality parameter by comparing each second signal quality parameter to a second quality threshold metric, wherein if the second signal quality parameter exceeds the second quality threshold metric, the QRS complex is identified as a valid QRS complex;
determining the occurrence or nonoccurrence of asystole and/or atrial fibrillation from the valid QRS complexes; and
causing an alarm to be displayed on a display component when asystole and/or atrial fibrillation is determined to occur.

Embodiment 2. A method according to embodiment 1, wherein the method comprises determining the occurrence or nonoccurrence of asystole, wherein asystole is determined to occur when no valid QRS complexes are identified over a predetermined time period.

Embodiment 3. A method according to embodiment 1 or 2, wherein the method comprises determining the occurrence or nonoccurrence of atrial fibrillation, wherein atrial fibrillation is determined by, for a plurality of pairs of consecutive valid QRS complexes occurring over a predetermined time period,
   for each consecutive pair of valid QRS complexes, determining an interval between a first fiducial point in the first member of the consecutive pair to a corresponding fiducial point in the first member of the consecutive pair, thereby providing a plurality of intervals,
   curating the plurality of intervals by calculating a third signal quality parameter for each interval and comparing each third signal quality parameter to a third quality threshold metric, wherein if the third signal quality parameter exceeds the third quality threshold metric, the interval is identified as a valid interval, and
   classifying whether the valid intervals obtained from the plurality of pairs of consecutive valid QRS complexes are indicative of atrial fibrillation.

Embodiment 4. A method according to embodiment 3, wherein the classifying step comprises calculating a root mean square of successive differences in the valid intervals.

Embodiment 5. A method according to embodiment 3 or 4, wherein the classifying step comprises calculating a sample entropy of successive differences in the valid intervals.

Embodiment 6. A method according to embodiment 3, wherein the classifying step comprises calculating a two dimensional space that is a function of a root mean square of successive differences in the valid intervals and a sample entropy of successive differences in the valid intervals, and defining values that fall within an area within the two dimensional space as being indicative of the occurrence of atrial fibrillation.

Embodiment 7. A method according to one of embodiments 1-6, wherein the method further comprises determining the occurrence or nonoccurrence of ventricular fibrillation/tachycardia by
processing at least two of the plurality of time-dependent ECG waveforms by
   selecting from each of the at least two ECG waveforms, a first waveform segment of time length t, and a second waveform segment of time length t, wherein the first and second waveform segments are non-overlapping consecutive segments, and
   for each of the first and second waveform segments, calculating a four-dimensional feature space comprising at least one temporal feature, at least one spectral feature, and at least one a complexity feature;

for each of the at least two ECG waveforms, determining if the four-dimensional feature space is indicative of the occurrence of ventricular fibrillation/tachycardia, wherein if ventricular fibrillation/tachycardia is indicated by processing of each of the at least two ECG waveforms, the occurrence ventricular fibrillation/tachycardia is determined; and cause an alarm to be displayed on a display component when ventricular fibrillation/tachycardia is determined to occur.

Embodiment 8. A method according to embodiment 7, wherein the four-dimensional feature space comprises threshold crossing sample count (TCSC), VF filter (VFleak), sample entropy, and Count2 features.

Embodiment 9. A method according to one of embodiments 1-8, wherein the first signal quality parameter is a kurtosis value calculated for each waveform in the plurality of waveforms.

Embodiment 10. A method according to embodiment 9, wherein the kurtosis value for each waveform in the plurality of waveforms is calculated from a time window of a predetermined length in each waveform.

Embodiment 11. The method of embodiment 9 or 10, wherein the kurtosis value for each waveform is updated at an interval of between 2 and 20 seconds, and preferably about every 3 to about every 5 seconds.

Embodiment 12. A method according to one of embodiments 1-11, wherein the second signal quality parameter is determined using a cliff amplitude and an elapsed time since the previous valid QRS complex identified.

Embodiment 13. A method according to one of embodiments 1-12, wherein each QRS complex in the combined ECG waveform is determined using a Pan-Tompkins algorithm.

Embodiment 14. A method according to one of embodiments 1-13, further comprising determining an activity type or activity level for the patient using time-dependent motion waveforms obtained from one or more accelerometers worn on the patient's body, and if the occurrence of asystole and/or atrial fibrillation is determined,
  determining if the activity type or activity level is inconsistent with the occurrence of asystole and/or atrial fibrillation and, if so, causing the alarm to be displayed on a display component to be modified.

Embodiment 15. A method according to embodiment 14, wherein the alarm is modified by being suppressed during the period of inconsistency.

Embodiment 16. A method according to embodiment 14, wherein the alarm is modified by requiring multiple consecutive asystole and/or atrial fibrillation determinations be identified in order for the alarm to be displayed on the display component.

Embodiment 17. A method according to one of embodiments 1-16, further comprising determining a photoplethysmogram for the patient using time-dependent optical waveforms obtained from an optical sensor worn on the patient's body, and if the occurrence of asystole and/or atrial fibrillation is determined,
  determining if the photoplethysmogram is inconsistent with the occurrence of asystole and/or atrial fibrillation and, if so, causing the alarm to be displayed on a display component to be modified.

Embodiment 18. A method according to embodiment 17, wherein the alarm is modified by being suppressed during the period of inconsistency.

Embodiment 19. A method according to embodiment 17, wherein the alarm is modified by requiring multiple consecutive asystole and/or atrial fibrillation determinations be identified in order for the alarm to be displayed on the display component.

Embodiment 20. A method according to one of embodiments 7-19, further comprising determining an activity type or activity level for the patient using time-dependent motion waveforms obtained from one or more accelerometers worn on the patient's body, and if the occurrence of ventricular fibrillation/tachycardia is determined,
  determining if the activity type or activity level is inconsistent with the occurrence of ventricular fibrillation/tachycardia and, if so, causing the alarm to be displayed on a display component to be modified.

Embodiment 21. A method according to embodiment 20, wherein the alarm is modified by being suppressed during the period of inconsistency.

Embodiment 22. A method according to embodiment 20, wherein the alarm is modified by requiring multiple consecutive asystole and/or atrial fibrillation determinations be identified in order for the alarm to be displayed on the display component.

Embodiment 23. A method according to one of embodiments 7-22, further comprising determining a photoplethysmogram for the patient using time-dependent optical waveforms obtained from an optical sensor worn on the patient's body, and if the occurrence of ventricular fibrillation/tachycardia is determined,
  determining if the photoplethysmogram is inconsistent with the occurrence of ventricular fibrillation/tachycardia and, if so, causing the alarm to be displayed on a display component to be modified.

Embodiment 24. A method according to embodiment 23, wherein the alarm is modified by being suppressed during the period of inconsistency.

Embodiment 25. A method according to embodiment 23, wherein the alarm is modified by requiring multiple consecutive asystole and/or atrial fibrillation determinations be identified in order for the alarm to be displayed on the display component.

Embodiment 26. A system for continuously monitoring a patient for cardiac electrical abnormalities, comprising:

an ECG sensor comprising plurality of ECG electrodes configured to be worn on the patient's body, the sensor configured to generate a plurality of time-dependent ECG waveforms, each waveform in the plurality of waveforms corresponding to electrical signals obtained from one ECG electrode in the plurality of ECG electrodes;

a processing component configured to receive and process the plurality of time-dependent ECG waveforms by
  determining a time-dependent first signal quality parameter for each waveform in the plurality of waveforms and curating the plurality of waveforms by comparing each first signal quality parameter to a first quality threshold metric,
  wherein if at least one first signal quality parameter exceeds the first quality threshold metric, accepting those waveforms having a first signal quality parameter that exceed the first quality threshold metric and discarding those waveforms having a first signal quality parameter that does not exceed the first quality threshold metric, or if no first signal quality parameter exceeds the first quality threshold metric, accepting all waveforms, and combining the accepted waveforms to provide a time-dependent combined ECG waveform;

the processing component further configured to process the combined ECG waveform to by identifying each QRS complex in the combined ECG waveform, determining a second signal quality parameter for each QRS complex by gravity cliff detection, curating each second signal quality parameter by comparing each second signal quality parameter to a second quality threshold metric, wherein if the second signal quality parameter exceeds the second quality threshold metric, the QRS complex is identified as a valid QRS complex;

determining the occurrence or nonoccurrence of asystole and/or atrial fibrillation from the valid QRS complexes; and cause an alarm to be displayed on a display component when asystole and/or atrial fibrillation is determined to occur.

Embodiment 27. A system according to embodiment 26, wherein the processing component is configured to determine the occurrence or nonoccurrence of asystole, wherein asystole is determined to occur when no valid QRS complexes are identified over a predetermined time period.

Embodiment 28. A system according to embodiment 26 or 27, wherein the processing component is configured to determine the occurrence or nonoccurrence of atrial fibrillation, wherein the processing component determines atrial fibrillation by, for a plurality of pairs of consecutive valid QRS complexes occurring over a predetermined time period, for each consecutive pair of valid QRS complexes, determining an interval between a first fiducial point in the first member of the consecutive pair to a corresponding fiducial point in the first member of the consecutive pair, thereby providing a plurality of intervals, curating the plurality of intervals by calculating a third signal quality parameter for each interval and comparing each third signal quality parameter to a third quality threshold metric, wherein if the third signal quality parameter exceeds the third quality threshold metric, the interval is identified as a valid interval, and classifying whether the valid intervals obtained from the plurality of pairs of consecutive valid QRS complexes are indicative of atrial fibrillation.

Embodiment 29. A system according to embodiment 28, wherein the classifying step comprises using the processing component to calculate a root mean square of successive differences in the valid intervals.

Embodiment 30. A system according to embodiment 28 or 29, wherein the classifying step comprises using the processing component to calculate a sample entropy of successive differences in the valid intervals.

Embodiment 31. A system according to embodiment 28, wherein the classifying step comprises using the processing component to calculate a two dimensional space that is a function of a root mean square of successive differences in the valid intervals and a sample entropy of successive differences in the valid intervals, and to define values that fall within an area within the two dimensional space as being indicative of the occurrence of atrial fibrillation.

Embodiment 32. A system according to one of embodiments 26-31, wherein the processing component is further configured to determine the occurrence or nonoccurrence of ventricular fibrillation/tachycardia by processing at least two of the plurality of time-dependent ECG waveforms by selecting from each of the at least two ECG waveforms, a first waveform segment of time length t, and a second waveform segment of time length t, wherein the first and second waveform segments are non-overlapping consecutive segments, and for each of the first and second waveform segments, calculating a four-dimensional feature space comprising at least one temporal feature, at least one spectral feature, and at least one a complexity feature;

for each of the at least two ECG waveforms, determining if the four-dimensional feature space is indicative of the occurrence of ventricular fibrillation/tachycardia, wherein if ventricular fibrillation/tachycardia is indicated by processing of each of the at least two ECG waveforms, the occurrence ventricular fibrillation/tachycardia is determined; and causing an alarm to be displayed on a display component when ventricular fibrillation/tachycardia is determined is determined to occur.

Embodiment 33. A system according to embodiment 32, wherein the four-dimensional feature space comprises threshold crossing sample count (TCSC), VF filter (VFleak), sample entropy, and Count2 features.

Embodiment 34. A system according to one of embodiments 26-33, wherein the first signal quality parameter is a kurtosis value calculated for each waveform in the plurality of waveforms.

Embodiment 35. A system according to embodiment 34, wherein the kurtosis value for each waveform in the plurality of waveforms is calculated from a time window of a predetermined length in each waveform.

Embodiment 36. The system of embodiment 34 or 36, wherein the kurtosis value for each waveform is updated at an interval of between 2 and 20 seconds, and preferably about every 3 to about every 5 seconds.

Embodiment 37. A system according to one of embodiments 26-36, wherein the second signal quality parameter is determined using a cliff amplitude and an elapsed time since the previous valid QRS complex identified.

Embodiment 38. A system according to one of embodiments 26-37, wherein each QRS complex in the combined ECG waveform is determined using a Pan-Tompkins algorithm.

Embodiment 39. A system according to one of embodiments 26-38, further comprising one or more accelerometers configured to be worn on the patient's body and generate one or more time-dependent motion waveforms indicative of patient motion, wherein the processing component if configured to receive and process the one or more time-dependent motion waveforms to determine an activity type or activity level for the patient, wherein if the occurrence of asystole and/or atrial fibrillation is determined, the processing component is further configured to determine if the activity type or activity level is inconsistent with the occurrence of asystole and/or atrial fibrillation and, if so, cause the alarm to be displayed on a display component to be modified.

Embodiment 40. A system according to embodiment 39, wherein the alarm is modified by being suppressed during the period of inconsistency.

Embodiment 41. A system according to embodiment 39, wherein the alarm is modified by requiring multiple consecutive asystole and/or atrial fibrillation determinations be identified in order for the alarm to be displayed on the display component.

Embodiment 42. A system according to one of embodiments 32-41, further comprising an optical sensor configured to be worn on the patient's body and generate a time-dependent plethysmogram waveform, wherein the processing component if configured to receive and process the time-dependent plethysmogram waveform for the patient, wherein if the occurrence of asystole and/or atrial fibrillation is determined, the processing component is further configured to determine if the plethysmogram waveform is inconsistent with the occurrence of asystole and/or atrial fibrillation and, if so, cause the alarm to be displayed on a display component to be modified.

Embodiment 43. A system according to embodiment 42, wherein the alarm is modified by being suppressed during the period of inconsistency.

Embodiment 44. A system according to embodiment 42, wherein the alarm is modified by requiring multiple consecutive asystole and/or atrial fibrillation determinations be identified in order for the alarm to be displayed on the display component.

Embodiment 45. A method for determining the occurrence or nonoccurrence of ventricular fibrillation/tachycardia, comprising:

obtaining a plurality of time-dependent electrocardiogram (ECG) waveforms from an ECG sensor comprising plurality of ECG electrodes, each waveform in the plurality of waveforms corresponding to electrical signals obtained from one ECG electrode in the plurality of ECG electrodes;

processing at least two of the plurality of time-dependent ECG waveforms by
  selecting from each of the at least two ECG waveforms, a first waveform segment of time length t, and a second waveform segment of time length t, wherein the first and second waveform segments are non-overlapping consecutive segments, and
  for each of the first and second waveform segments, calculating a four-dimensional feature space comprising at least one temporal feature, at least one spectral feature, and at least one a complexity feature;

for each of the at least two ECG waveforms, determining if the four-dimensional feature space is indicative of the occurrence of ventricular fibrillation/tachycardia, wherein if ventricular fibrillation/tachycardia is indicated by processing of each of the at least two ECG waveforms, the occurrence ventricular fibrillation/tachycardia is determined; and cause an alarm to be displayed on a display component when ventricular fibrillation/tachycardia is determined to occur.

Embodiment 46. A method according to embodiment 45, wherein the four-dimensional feature space comprises threshold crossing sample count (TCSC), VF filter (VFleak), sample entropy, and Count2 features.

Embodiment 47. A method according to one of embodiments 45 or 46, further comprising determining an activity type or activity level for the patient using time-dependent motion waveforms obtained from one or more accelerometers worn on the patient's body, and if the occurrence of ventricular fibrillation/tachycardia is determined,
  determining if the activity type or activity level is inconsistent with the occurrence of ventricular fibrillation/tachycardia and, if so, causing the alarm to be displayed on a display component to be modified.

Embodiment 48. A method according to embodiment 47, wherein the alarm is modified by being suppressed during the period of inconsistency.

Embodiment 49. A method according to embodiment 47, wherein the alarm is modified by requiring multiple consecutive asystole and/or atrial fibrillation determinations be identified in order for the alarm to be displayed on the display component.

Embodiment 50. A method according to one of embodiments 45-49, further comprising determining a photoplethysmogram for the patient using time-dependent optical waveforms obtained from an optical sensor worn on the patient's body, and if the occurrence of ventricular fibrillation/tachycardia is determined,
  determining if the photoplethysmogram is inconsistent with the occurrence of ventricular fibrillation/tachycardia and, if so, causing the alarm to be displayed on a display component to be modified.

Embodiment 51. A method according to embodiment 50, wherein the alarm is modified by being suppressed during the period of inconsistency.

Embodiment 52. A method according to embodiment 50, wherein the alarm is modified by requiring multiple consecutive asystole and/or atrial fibrillation determinations be identified in order for the alarm to be displayed on the display component.

Embodiment 53. A system for continuously monitoring a patient for cardiac electrical abnormalities, comprising:

an ECG sensor comprising plurality of ECG electrodes configured to be worn on the patient's body, the sensor configured to generate a plurality of time-dependent ECG waveforms, each waveform in the plurality of waveforms corresponding to electrical signals obtained from one ECG electrode in the plurality of ECG electrodes;

a processing component configured to receive and process the plurality of time-dependent ECG waveforms by
  selecting from each of the at least two ECG waveforms, a first waveform segment of time length t, and a second waveform segment of time length t, wherein the first and second waveform segments are non-overlapping consecutive segments, and
  for each of the first and second waveform segments, calculating a four-dimensional feature space comprising at least one temporal feature, at least one spectral feature, and at least one a complexity feature;

for each of the at least two ECG waveforms, determining if the four-dimensional feature space is indicative of the occurrence of ventricular fibrillation/tachycardia, wherein if ventricular fibrillation/tachycardia is indicated by processing of each of the at least two ECG waveforms, the occurrence ventricular fibrillation/tachycardia is determined; and cause an alarm to be displayed on a display component when ventricular fibrillation/tachycardia is determined to occur.

Embodiment 54. A system according to embodiment 53, wherein the four-dimensional feature space comprises threshold crossing sample count (TCSC), VF filter (VFleak), sample entropy, and Count2 features.

Embodiment 55. A system according to one of embodiments 53 or 54, further comprising one or more accelerometers configured to be worn on the patient's body and generate one or more time-dependent motion waveforms indicative of patient motion, wherein the processing component if configured to receive and process the one or more time-dependent motion waveforms to determine an activity type or activity level for the patient, wherein if the occurrence of asystole and/or atrial fibrillation is determined, the processing component is further configured to determine if the activity type or activity level is inconsistent with the occurrence of asystole and/or atrial fibrillation and, if so, cause the alarm to be displayed on a display component to be modified.

Embodiment 56. A system according to embodiment 55, wherein the alarm is modified by being suppressed during the period of inconsistency.

Embodiment 57. A system according to embodiment 55, wherein the alarm is modified by requiring multiple consecutive asystole and/or atrial fibrillation determinations be identified in order for the alarm to be displayed on the display component.

Embodiment 58. A system according to one of embodiments 53-57, further comprising an optical sensor configured to be worn on the patient's body and generate a time-dependent plethysmogram waveform, wherein the processing component if configured to receive and process the time-dependent plethysmogram waveform for the patient, wherein if the occurrence of asystole and/or atrial fibrillation is determined, the processing component is further configured to determine if the plethysmogram waveform is inconsistent with the occurrence of asystole and/or atrial fibrillation and, if so, cause the alarm to be displayed on a display component to be modified.

Embodiment 59. A system according to embodiment 58, wherein the alarm is modified by being suppressed during the period of inconsistency.

Embodiment 60. A system according to embodiment 58, wherein the alarm is modified by requiring multiple consecutive asystole and/or atrial fibrillation determinations be identified in order for the alarm to be displayed on the display component.

The following references are incorporated by reference in their entirety.

Tabakov S, Iliev I, Krasteva V. Online Digital Filter and QRS Detector Applicable in Low Resource ECG Monitoring Systems. Annals of Biomedical Engineering; Vol. 36, No. 11, 2008:1805-1815

Dash S, Chon K H, Lu S, Raeder E A. Automatic Real Time Detection of Atrial Fibrillation. Annals of Biomedical Engineering; Vol. 37, No. 9, 2009:1701-1709.

Alcaraz R, Rieta J J. A review on sample entropy applications of the non-invasive analysis of atrial fibrillation electrocardiograms. Biomedical Signal Processing and Control; Vol. 5, 2010:1-14.

Li Q, Rajagopalan C, Clifford G. Ventricular Fibrillation and Tachycardia Classification Using a Machine Learning Approach. IEEE Transactions on Biomedical Engineering; Vol. 61, No 6, June 2014:1607-1613.

Jekova I, Krasteva V. Real Time detection of ventricular fibrillation and tachycardia. Physiologic Measurement; Vol. 25, 2004: 1167-1178.

Arafat M A, Chowdhurry A W, Hasan K. A simple time domain algorithm for detection of ventricular fibrillation in electrocardiogram. Signal, Image, and Video Processing; Vol. 5, 2011: 1-10.

Jekova I. Shock advisory tool: Detection of life threatening cardiac arrhythmias and shock success prediction by means of a common parameter set. Biomedical Signal Processing and Control; Vol. 2, 2007: 25-33.

Li H, Han W, Hu C, Max Q. Detecting Ventricular Fibrillation by Fast Algorithm of Dynamic Sample Entropy. Proceedings of the 2009 IEEE International Conference on Robotics and Biomimetics; 2009: 1105-1110.

Zhu J, Rosset S, Zou H, Hastie T. Multi-class AdaBoost. Statistics And Its Interface; Vol. 2, 2009: 349-360.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for continuously monitoring a patient for cardiac electrical abnormalities, comprising:

obtaining a plurality of time-dependent electrocardiogram (ECG) waveforms from an ECG sensor comprising plurality of ECG electrodes, each waveform in the plurality of waveforms corresponding to electrical signals obtained from one ECG electrode in the plurality of ECG electrodes;

processing the plurality of waveforms by
determining a time-dependent first signal quality parameter for each waveform in the plurality of waveforms and curating the plurality of waveforms by comparing each first signal quality parameter to a first quality threshold metric,
wherein if at least one first signal quality parameter exceeds the first quality threshold metric, accepting those waveforms having a first signal quality parameter that exceed the first quality threshold metric and discarding those waveforms having a first signal quality parameter that does not exceed the first quality threshold metric, or if no first signal quality parameter exceeds the first quality threshold metric, accepting all waveforms, and combining the accepted waveforms to provide a time-dependent combined ECG waveform;

processing the combined ECG waveform to by
identifying each QRS complex in the combined ECG waveform,
determining a second signal quality parameter for each QRS complex by gravity cliff detection, and
curating each second signal quality parameter by comparing each second signal quality parameter to a second quality threshold metric, wherein if the second signal quality parameter exceeds the second quality threshold metric, the QRS complex is identified as a valid QRS complex;

determining the occurrence or nonoccurrence of asystole and/or atrial fibrillation from the valid QRS complexes; and causing an alarm to be displayed on a display component when asystole and/or atrial fibrillation is determined to occur.

2. A method according to claim 1, wherein the method further comprises determining the occurrence or nonoccurrence of ventricular fibrillation/tachycardia by
processing at least two of the plurality of time-dependent ECG waveforms by
selecting from each of the at least two ECG waveforms, a first waveform segment of time length t, and a second waveform segment of time length t, wherein the first and second waveform segments are non-overlapping consecutive segments, and
for each of the first and second waveform segments, calculating a four-dimensional feature space comprising at least one temporal feature, at least one spectral feature, and at least one a complexity feature;
for each of the at least two ECG waveforms, determining if the four-dimensional feature space is indicative of the occurrence of ventricular fibrillation/tachycardia, wherein if ventricular fibrillation/tachycardia is indicated by processing of each of the at least two ECG waveforms, the occurrence ventricular fibrillation/tachycardia is determined; and
cause an alarm to be displayed on a display component when ventricular fibrillation/tachycardia is determined to occur.

3. A method according to claim 2, further comprising determining an activity type or activity level for the patient using time-dependent motion waveforms obtained from one or more accelerometers worn on the patient's body, and if the occurrence of ventricular fibrillation/tachycardia is determined,
determining if the activity type or activity level is inconsistent with the occurrence of ventricular fibrillation/tachycardia and, if so, causing the alarm to be displayed on a display component to be modified.

4. A method according to claim 3, wherein the alarm is modified by being suppressed during the period of inconsistency.

5. A method according to claim 3, wherein the alarm is modified by requiring multiple consecutive asystole and/or atrial fibrillation determinations be identified in order for the alarm to be displayed on the display component.

6. A method according to claim 2, further comprising determining a photoplethysmogram for the patient using time-dependent optical waveforms obtained from an optical sensor worn on the patient's body, and if the occurrence of ventricular fibrillation/tachycardia is determined,
determining if the photoplethysmogram is inconsistent with the occurrence of ventricular fibrillation/tachycardia and, if so, causing the alarm to be displayed on a display component to be modified.

7. A method according to claim 6, wherein the alarm is modified by being suppressed during the period of inconsistency.

8. A method according to claim 6, wherein the alarm is modified by requiring multiple consecutive asystole and/or atrial fibrillation determinations be identified in order for the alarm to be displayed on the display component.

9. A method according to claim 2, wherein the four-dimensional feature space comprises threshold crossing sample count (TCSC), VF filter (VFleak), sample entropy, and Count2 features.

10. A method according to claim 1, wherein the first signal quality parameter is a kurtosis value calculated for each waveform in the plurality of waveforms.

11. A method according to claim 10, wherein the kurtosis value for each waveform in the plurality of waveforms is calculated from a time window of a predetermined length in each waveform.

12. The method of claim 11, wherein the kurtosis value for each waveform is updated at an interval of between 2 and 20 seconds, and preferably about every 3 to about every 5 seconds.

13. A method according to claim 10, wherein the second signal quality parameter is determined using a cliff amplitude and an elapsed time since the previous valid QRS complex identified.

14. A method according to claim 1, wherein the method comprises determining the occurrence or nonoccurrence of atrial fibrillation, wherein atrial fibrillation is determined by, for a plurality of pairs of consecutive valid QRS complexes occurring over a predetermined time period,
for each consecutive pair of valid QRS complexes, determining an interval between a first fiducial point in the first member of the consecutive pair to a corresponding fiducial point in the first member of the consecutive pair, thereby providing a plurality of intervals,
curating the plurality of intervals by calculating a third signal quality parameter for each interval and comparing each third signal quality parameter to a third quality threshold metric, wherein if the third signal quality parameter exceeds the third quality threshold metric, the interval is identified as a valid interval, and
classifying whether the valid intervals obtained from the plurality of pairs of consecutive valid QRS complexes are indicative of atrial fibrillation.

15. A method according to claim 14, wherein the classifying step comprises calculating a root mean square of successive differences in the valid intervals.

16. A method according to claim 14, wherein the classifying step comprises calculating a sample entropy of successive differences in the valid intervals.

17. A method according to claim 14, wherein the classifying step comprises calculating a two dimensional space that is a function of a root mean square of successive differences in the valid intervals and a sample entropy of successive differences in the valid intervals, and defining values that fall within an area within the two dimensional space as being indicative of the occurrence of atrial fibrillation.

18. A method according to claim 1, further comprising determining an activity type or activity level for the patient using time-dependent motion waveforms obtained from one or more accelerometers worn on the patient's body, and if the occurrence of asystole and/or atrial fibrillation is determined,
determining if the activity type or activity level is inconsistent with the occurrence of asystole and/or atrial fibrillation and, if so, causing the alarm to be displayed on a display component to be modified.

19. A method according to claim 18, wherein the alarm is modified by being suppressed during the period of inconsistency.

20. A method according to claim 18, wherein the alarm is modified by requiring multiple consecutive asystole and/or atrial fibrillation determinations be identified in order for the alarm to be displayed on the display component.

21. A method according to claim 1, further comprising determining a photoplethysmogram for the patient using time-dependent optical waveforms obtained from an optical sensor worn on the patient's body, and if the occurrence of asystole and/or atrial fibrillation is determined,
determining if the photoplethysmogram is inconsistent with the occurrence of asystole and/or atrial fibrillation and, if so, causing the alarm to be displayed on a display component to be modified.

22. A method according to claim 21, wherein the alarm is modified by being suppressed during the period of inconsistency.

23. A method according to claim 21, wherein the alarm is modified by requiring multiple consecutive asystole and/or atrial fibrillation determinations be identified in order for the alarm to be displayed on the display component.

24. A method according to claim 1, wherein the method comprises determining the occurrence or nonoccurrence of asystole, wherein asystole is determined to occur when no valid QRS complexes are identified over a predetermined time period.

25. A method according to claim 1, wherein each QRS complex in the combined ECG waveform is determined using a Pan-Tompkins algorithm.

26. A system for continuously monitoring a patient for cardiac electrical abnormalities, comprising:
an ECG sensor comprising plurality of ECG electrodes configured to be worn on the patient's body, the sensor configured to generate a plurality of time-dependent ECG waveforms, each waveform in the plurality of waveforms corresponding to electrical signals obtained from one ECG electrode in the plurality of ECG electrodes;
a processing component configured to receive and process the plurality of time-dependent ECG waveforms by
determining a time-dependent first signal quality parameter for each waveform in the plurality of waveforms and curating the plurality of waveforms by comparing each first signal quality parameter to a first quality threshold metric,
wherein if at least one first signal quality parameter exceeds the first quality threshold metric, accepting those waveforms having a first signal quality parameter that exceed the first quality threshold metric and discarding those waveforms having a first signal quality parameter that does not exceed the first quality threshold metric, or if no first signal quality parameter exceeds the first quality threshold metric, accepting all waveforms, and
combining the accepted waveforms to provide a time-dependent combined ECG waveform;
the processing component further configured to process the combined ECG waveform to by
identifying each QRS complex in the combined ECG waveform,
determining a second signal quality parameter for each QRS complex by gravity cliff detection,
curating each second signal quality parameter by comparing each second signal quality parameter to a second quality threshold metric, wherein if the second signal quality parameter exceeds the second quality threshold metric, the QRS complex is identified as a valid QRS complex;
determining the occurrence or nonoccurrence of asystole and/or atrial fibrillation from the valid QRS complexes; and
cause an alarm to be displayed on a display component when asystole and/or atrial fibrillation is determined to occur.

* * * * *